US012220515B2

(12) United States Patent
Federspiel et al.

(10) Patent No.: US 12,220,515 B2
(45) Date of Patent: Feb. 11, 2025

(54) MODULAR EXTRACORPOREAL AMBULATORY LUNG ASSIST DEVICE

(71) Applicants: University of Pittsburgh—Of the Commonwealth System of Higher Education, Pittsburgh, PA (US); Mississippi State University, Starkville, MS (US)

(72) Inventors: William J. Federspiel, Pittsburgh, PA (US); Shalv Madhani, Costa Mesa, CA (US); Ryan A. Orizondo, Pittsburgh, PA (US); Peter Drew Wearden, Orlando, FL (US); Brian Joseph Frankowski, Imperial, PA (US); Alexandra May, Miami, FL (US); Gregory Burgreen, Starkville, MS (US)

(73) Assignees: University of Pittsburgh—Of the Commonwealth System of Higher Education, Pittsburgh, PA (US); Mississippi State University, Starkville, MS (US)

( * ) Notice: Subject to any disclaimer, the term of this patent is extended or adjusted under 35 U.S.C. 154(b) by 1054 days.

(21) Appl. No.: 16/961,440

(22) PCT Filed: Jan. 15, 2019

(86) PCT No.: PCT/US2019/013678
§ 371 (c)(1),
(2) Date: Jul. 10, 2020

(87) PCT Pub. No.: WO2019/143623
PCT Pub. Date: Jul. 25, 2019

(65) Prior Publication Data
US 2021/0077706 A1    Mar. 18, 2021
US 2022/0080095 A2    Mar. 17, 2022

Related U.S. Application Data

(60) Provisional application No. 62/617,809, filed on Jan. 16, 2018.

(51) Int. Cl.
*A61M 1/36* (2006.01)
*A61M 1/16* (2006.01)
(Continued)

(52) U.S. Cl.
CPC ........ *A61M 1/3667* (2014.02); *A61M 1/1625* (2014.02); *A61M 1/1698* (2013.01);
(Continued)

(58) Field of Classification Search
CPC .............. A61M 1/3667; A61M 1/1625; A61M 1/1698; A61M 60/113; A61M 60/216;
(Continued)

(56) References Cited

U.S. PATENT DOCUMENTS 4,239,729 A    12/1980    Hasegawa
5,263,924 A    11/1993    Mathewson
(Continued)

FOREIGN PATENT DOCUMENTS

EP    0264696 A2    4/1988
EP    1930034    6/2008
(Continued)

OTHER PUBLICATIONS

Wu, Z. J., et al., Progress toward an ambulatory pump-lung. The Journal of thoracic and cardiovascular surgery, 2005, 130(4), 973-978.
(Continued)

*Primary Examiner* — Susan S Su
*Assistant Examiner* — Katherine-Ph Minh Pham
(74) *Attorney, Agent, or Firm* — BARTONY & ASSOCIATES, LLC

(57) ABSTRACT

A system for lung assist includes a plurality of fiber bundle sections. Each of the fiber bundle sections includes a fiber bundle housing defining a fiber bundle compartment therein and a fiber bundle positioned within the fiber bundle compartment. The fiber bundle includes a plurality of hollow gas permeable fibers configured to permit diffusion of gas between blood and an interior of the plurality of hollow gas permeable fibers. The plurality of hollow gas permeable fibers is positioned such that blood flows around the plurality of hollow gas permeable fibers when flowing through the fiber bundle compartment. Each fiber bundle is different in at least one property from each other fiber bundle. The fiber bundle housing further includes a gas inlet in fluid connection with the fiber bundle housing and in fluid connection with inlets of the plurality of hollow gas permeable fibers, a gas outlet in fluid connection with the housing and in fluid connection with outlets of the plurality of hollow gas permeable fibers, and a blood outlet in fluid connection with a first end of the fiber bundle. The fiber bundle housing also includes a first interface. The system further includes a base section including a housing including a pressurizing compartment, a pressurizing mechanism within the pressurizing compartment, a blood inlet in fluid connection with the pressurizing compartment and a conduit in fluid connection with the pressurizing compartment at a first end thereof via which pressurized fluid exits the pressurizing compartment. The base further includes a second interface adapted to form a releasable, sealing connection with the first interface of one of the plurality of fiber bundle sections. A second end of the conduit is placed in fluid connection with a second end of the fiber bundle when the fiber bundle section is connected to the base section via the first interface and the second interface.

20 Claims, 13 Drawing Sheets

(51) Int. Cl.
  *A61M 60/113* (2021.01)
  *A61M 60/216* (2021.01)
  *A61M 60/38* (2021.01)
  *A61M 60/825* (2021.01)

(52) U.S. Cl.
  CPC ........ *A61M 1/3623* (2022.05); *A61M 60/113* (2021.01); *A61M 60/216* (2021.01); *A61M 60/38* (2021.01); *A61M 60/825* (2021.01); *A61M 2202/0225* (2013.01); *A61M 2205/7536* (2013.01)

(58) Field of Classification Search
  CPC ................ A61M 60/38; A61M 60/825; A61M 2202/0225; A61M 2205/7536; A61M 2209/082; A61M 1/267; A61M 1/3623
  See application file for complete search history.

(56) References Cited

U.S. PATENT DOCUMENTS

| | | | |
|---|---|---|---|
| 5,290,236 | A | 3/1994 | Mathewson |
| 5,591,404 | A | 1/1997 | Mathewson |
| 5,695,471 | A | 12/1997 | Wampler |
| 5,770,149 | A | 6/1998 | Raible |
| 6,117,390 | A | 9/2000 | Corey, Jr. |
| 6,224,829 | B1 | 5/2001 | Piplani |
| 6,379,618 | B1 | 4/2002 | Piplani |
| 6,428,747 | B1 | 8/2002 | Dueri |
| 6,503,450 | B1 | 1/2003 | Afzal |
| 6,623,475 | B1 | 9/2003 | Siess |
| 6,723,284 | B1 | 4/2004 | Reeder |
| 7,022,284 | B2 | 4/2006 | Brian |
| 7,763,097 | B2 | 7/2010 | Federspiel |
| 7,871,566 | B2 | 1/2011 | Strauss |
| 8,133,195 | B2 | 3/2012 | Blicke |
| 8,187,216 | B2 | 5/2012 | Niitsuma |
| 10,080,834 | B2 | 9/2018 | Federspiel |
| 10,258,729 | B2 | 4/2019 | Gellman |
| 2002/0110485 | A1 | 8/2002 | Stringer |
| 2004/0052681 | A1* | 3/2004 | Mortensen .......... A61M 1/1625 604/6.14 |
| 2007/0249888 | A1 | 10/2007 | Wu |
| 2008/0199357 | A1 | 8/2008 | Gellman |
| 2013/0343954 | A1 | 12/2013 | Gartner |
| 2014/0065016 | A1 | 3/2014 | Federspiel |
| 2014/0288354 | A1 | 9/2014 | Timms |
| 2017/0100531 | A1 | 4/2017 | Madhani |
| 2019/0022300 | A1 | 1/2019 | Federspiel |

FOREIGN PATENT DOCUMENTS

| | | | |
|---|---|---|---|
| WO | WO1993005828 | | 4/1993 |
| WO | WO199959654 | | 11/1999 |
| WO | WO2006031858 | A1 | 3/2006 |
| WO | WO2006118817 | A1 | 11/2006 |
| WO | WO2009100336 | A1 | 8/2009 |
| WO | WO2014085620 | | 6/2014 |
| WO | WO-2014085620 | A1 * | 6/2014 .......... A61M 1/1698 |
| WO | WO2016054543 | A1 | 4/2016 |
| WO | WO2016210089 | | 12/2016 |
| WO | WO-2016210089 | A1 * | 12/2016 .......... A61M 1/1006 |
| WO | WO2019143623 | | 7/2019 |

OTHER PUBLICATIONS

Zhang, T. et al., A novel wearable pump-lung device: In vitro and acute in vivo study. The Journal of Heart and Lung Transplantation, (2012), 31(1), 101-105.
Wu, Z. J. et al., Thirty-day in-vivo performance of a wearable artificial pump-lung for ambulatory respiratory support. The Annals of thoracic surgery, (2012), 93(1), 274-281.
Schewe, R. E. et al., In-parallel attachment of a low-resistance compliant thoracic artificial lung under rest and simulated exercise. The Annals of thoracic surgery, (2012), 94(5), 1688-1694.
ASAIO 2015 Oral presentation in Chicago (Jun. 25, 2015).
Pacella, HE, et al., Permeability of hollow fiber bundles using in blood oxygenation devices. J of Membrane Sci. 382 (1-2): 238-242, 2011.
Zhang J, et al., . Characterization of membrane blood oxygenation devices using computational fluid dynamics. J. Membrane Sci 288:268-279, 2007.
Svitek RG, et al.; A mathematical model to predict CO2 removal in hollow fiber membrane oxygenators. Ann. Biomed. Eng. 36(6):992-1003, 2008.
Burgreen GW, Kameneva K. Hemolysis minimization using CFD-based design technology. ASAIO J. 50(2):171, 2004.
Whelan DM, Giessen WJ, Krabbendam SC, Vliet EA, Verdouw PD, Serruys PW, Beusekom HMM. Biocompatibility of phosphorylcholine coated stents in normal porcine coronary arteries. Heart, 83:338-345. 2000.
Hiromi Kitano, Hisatomo Suzuki, Kazuhiro Matsuura, and Kohji Ohno,,, Molecular recognition at the exterior surface of a zwitterionic telomer brush. Langmuir, 26(9):6767-6774.2010.
Yang W, Xue H, Carr LR, Wang J, Jiang S, Zwitterionic poly(carboxybetaine) hydrogels for glucose biosensors in complex media. Biosensors and Bioelectronics, 26:2454-245.2011.
Oh HI, Ye SH, Johnson CA Jr, Woolley Jr, Federspiel WJ and Wagner WR. Hemocompatibility assessment of carbonic anhydrase modified hollow fiber membranes for artificial lungs. Artificial Organs, 34 (5):439-442. 2010.
Holmlin RE, Chen X, Chapman RG, Takayama S, Whitesides GM.

(56) References Cited

OTHER PUBLICATIONS

Zwitterionic SAMs that resist nonspecific adsorption of protein from aqueous buffer. Langmuir, 17:2841-2850, 2001.

Okamoto T, Tashiro M, Sakanashi Y, et al.: A New Heparin-Bonded Dense Membrane Lung Combined with Minimal Systemic Heparinization Prolonged Extracorporeal Lung Assist in Goats. Artif Organs 22: 864-872, 1998.

Wu ZJ, Gellman B, Zhang T, Taskin ME, Dasse KA, Griffith BP: Computational Fluid Dynamics and Experimental Characterization of the Pediatric Pump-Lung Cardiovasc Eng Technol 2: 276-287, 2011.

Wei X, Sanchez PG, Liu Y, et al.: Extracorporeal Respiratory Support With a Miniature Integrated Pediatric Pump-Lung Device in an Acute Ovine Respiratory Failure Model: Respiratory Support with the PediPL Artif Organs 40: 1046-1053, 2016.

Liu Y, Sanchez PG, Wei X, et al.: Effects of Cardiopulmonary Support With a Novel Pediatric Pump-Lung in a 30-Day Ovine Animal Model: Evaluation of a Pediatric Pump-Lung Artif Organs 39: 989-997, 2015.

Zhang T, Cheng G, Koert A, et al.: Functional and Biocompatibility Performances of an Integrated Maglev Pump-Oxygenator Artif Organs 33: 36-45, 2009.

Wu ZJ, Taskin ME, Zhang T, Fraser KH, Griffith BP: Computational Model-Based Design of a Wearable Artificial Pump-Lung for Cardiopulmonary / Respiratory Support: Design of a Wearable Pump-Lung Artif Organs 36: 387-399, 2012.

Wang D, Lick SD, Campbell KM, et al.: Development of Ambulatory Arterio Venous Carbon Dioxide Removal (AVCO2R): The Downsized Gas Exchanger Prototype for Ambulation Removes Enough CO2 with Low Blood Resistance: ASAIO J 51: 385-389, 2005.

Madhani, Shalv P. et al, In vitro and in vivo evaluation of a novel integrated wearable artificial lung; The Journal of Heart and Lung Transplantation, 2017, col. 36, Issue 7, pp. 2-6.

Madhani, Shalv P. et al, Fiber Bundle Design for an Integrated Wearable Artificial Lung, ASAIO Journal, 2017, 63, pp. 631-636.

Madhani, Shalv P. et al, In Vivo 5 Day Animal Studies of a Compact, Wearable Pumping Artificial Lung, ASAIO Journal, 2017, 1-7.

Schewe, Rebecca E. et al., Design and In Vitro Assessment of an Improved, Low-Resistance, Compliant Thoracic Artificial Lung, ASAIO J. Nov. 2012 ; 58(6): 583-589.

Skoog, David J., et al; Fourteen Day In Vivo Testing of a Compliant Thoracic Artificial Lung (cTAL), ASAIO J. 2017 ; 63(5): 644-649.

\* cited by examiner

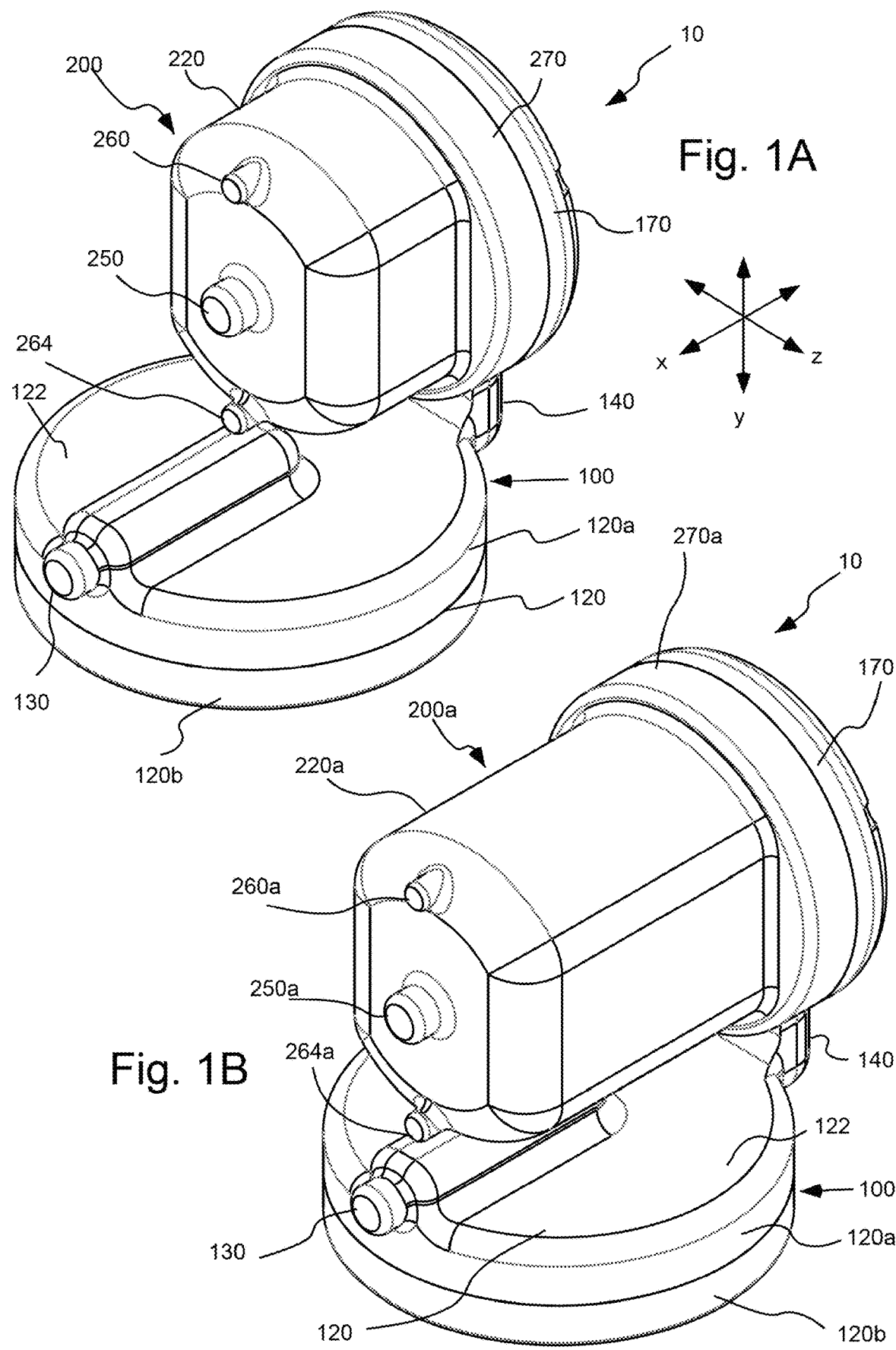

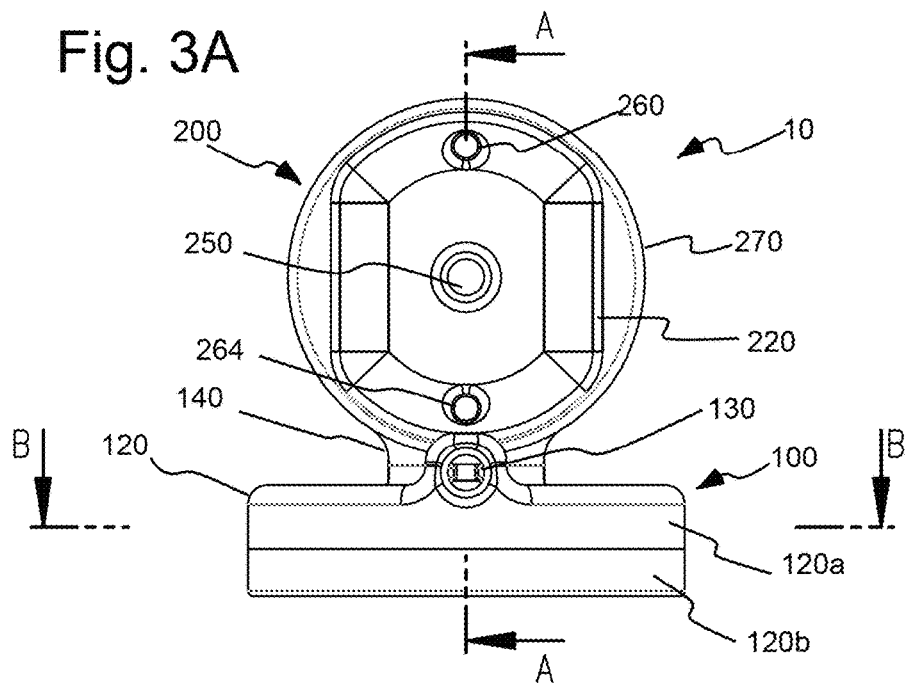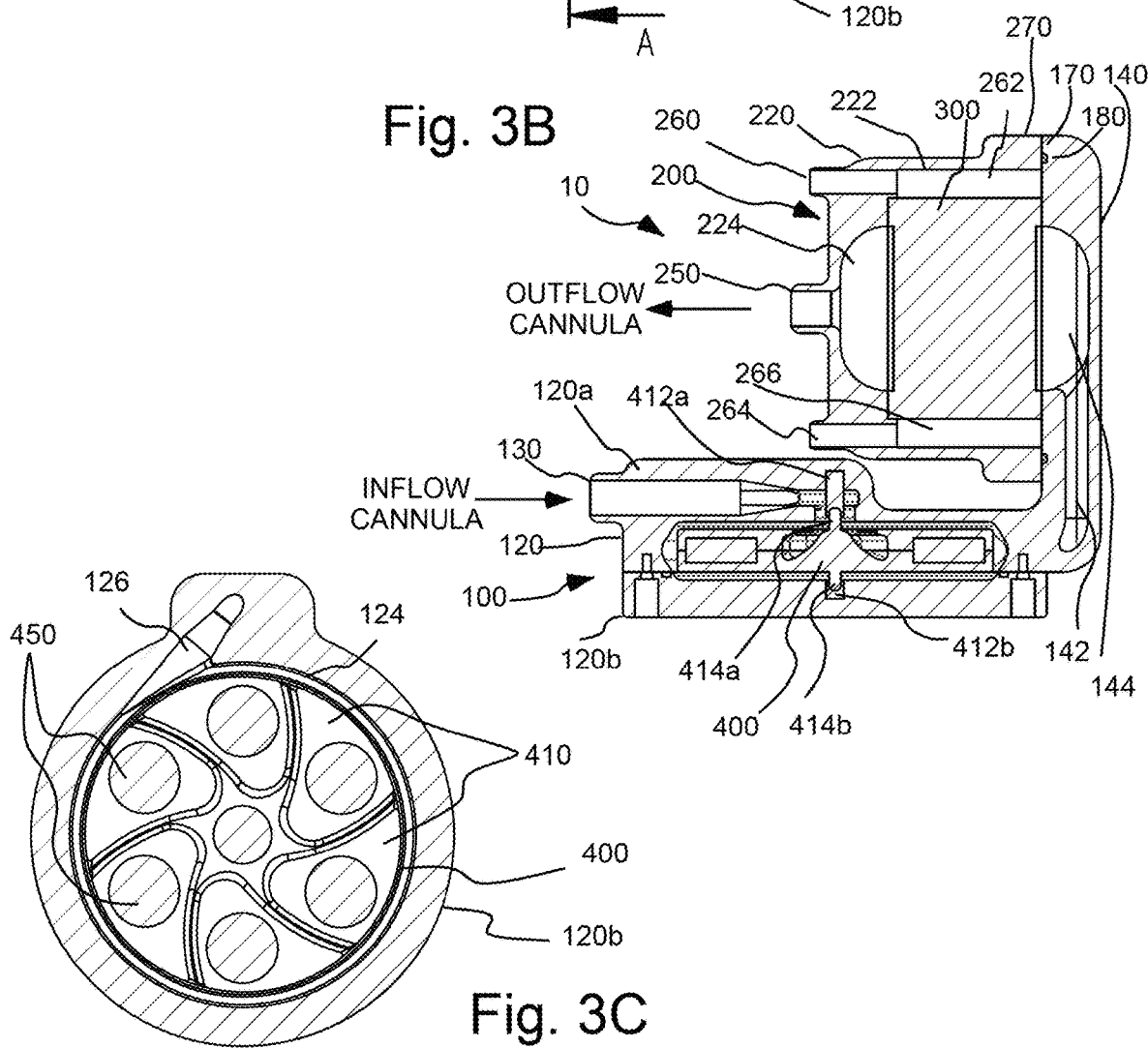

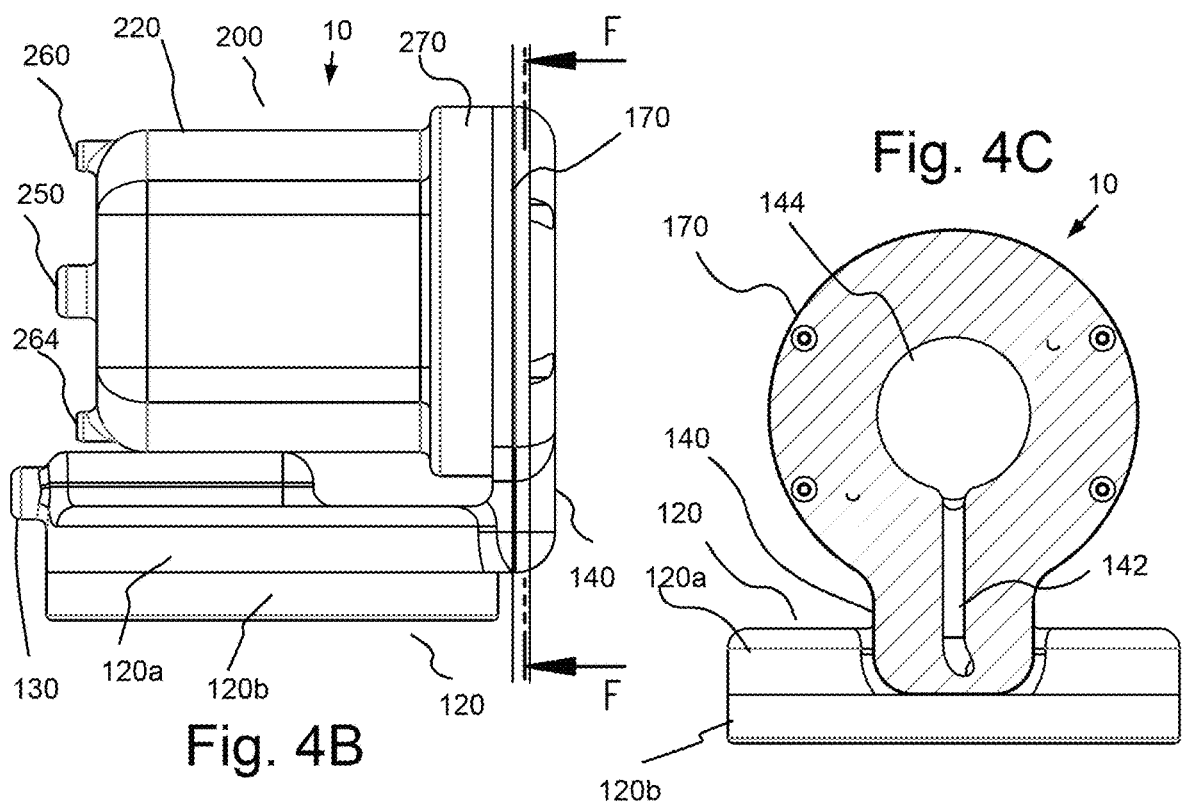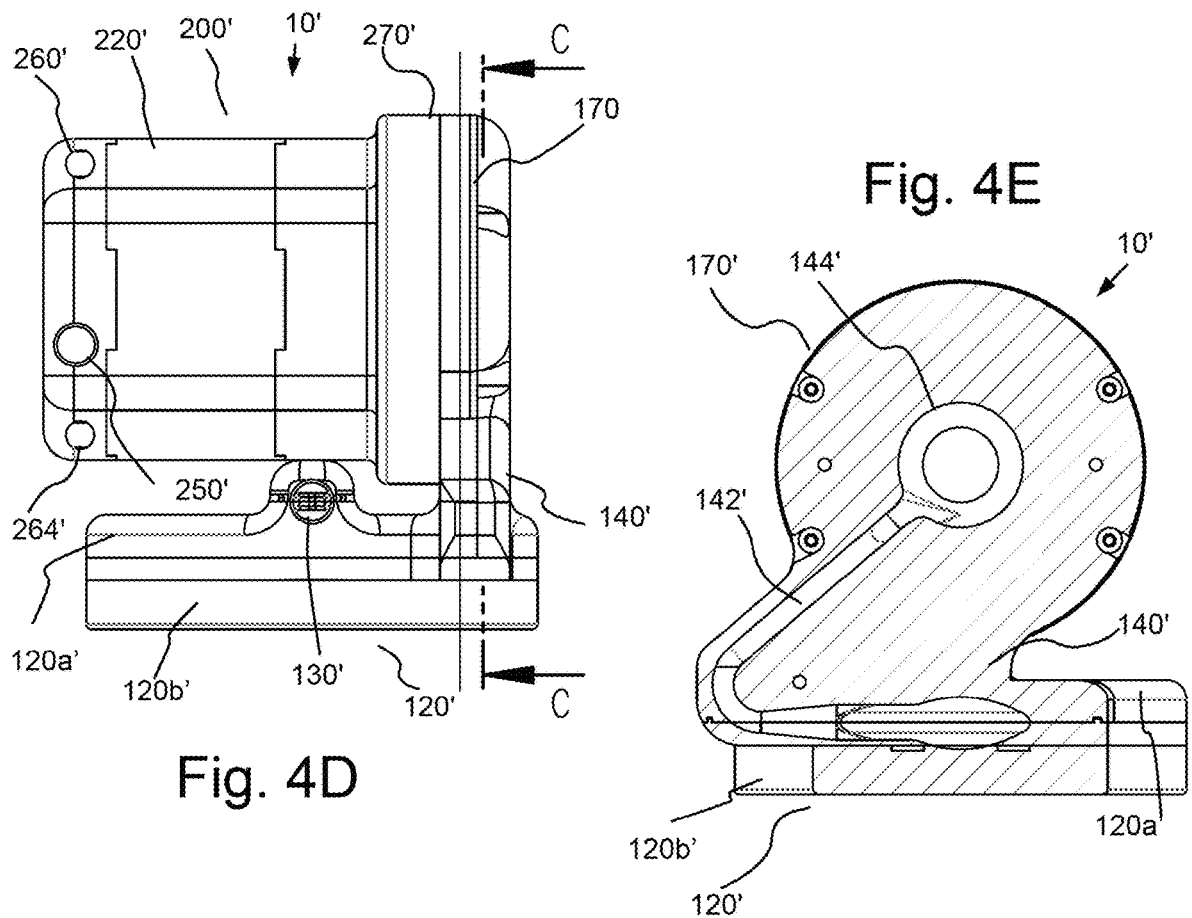

Device 10 with fiber bundle section 200 (0.3 sq meters)

*Pressure requirements assume 18 Fr venous cannula, 14 Fr arterial cannula, and a outflow (pulmonary artery) pressure of 50 mmHg due to pulmonary hypertension Device 10 with fiber bundle section 200a (0.65 sq meters)

*Pressure requirements assume 27 Fr dual-lumen cannula

Device 10 with fiber bundle section 200a (0.65 sq meters)

*Pressure requirements assume 15.5 Fr dual-lumen cannula

Device 10 with fiber bundle section 200 (0.3 sq meters)

*sweep gas flow rate = 5 L/min

MODULAR EXTRACORPOREAL AMBULATORY LUNG ASSIST DEVICE

CROSS-REFERENCE TO RELATED APPLICATIONS

This application is a national phase filing of PCT International Patent Application No. PCT/US2019/013678, filed Jan. 15, 2019, which claims benefit of U.S. Provisional Patent Application Ser. No. 62/617,809, filed Jan. 16, 2018, the disclosures of which are incorporated herein by reference.

GOVERNMENTAL INTEREST

This invention was made with government support under grant nos. HL117637 and HL135482 awarded by the National Institute of Health. The government has certain rights in this invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Lung disease, whether acute or chronic, are major healthcare problems. The American Lung Association reports that nearly 350,000 Americans die each year of some form of lung disease. Lung disease, which is responsible for one in seven deaths, is the number three killer of Americans. Acute lung failure and adult respiratory distress syndrome (ARDS) are prevalent forms of lung disease. ARDS afflicts about 150,000 Americans each year. The associated mortality of ARDS remains between 40 and 60% despite improvements in critical care medicine.

Most lung disease, however, is chronic. Emphysema and chronic bronchitis, two forms of chronic obstructive pulmonary disease (COPD), afflict over 14 million Americans annually. Chronic lung disease is now the 3rd leading cause of death in America, claiming the lives of over 400,000 annually and carrying a cost of $154 billion. As chronic lung disease reaches end stage, lung transplantation becomes the only choice for effective treatment. Lung transplantation has had a steady rise over the last 10 years and ~3300 lung transplants are performed annually worldwide. The average time on the waiting list varies from 6 to 12 months depending on the patient's condition and institutional expertise, and 10-15% of patients die while on the waiting list in the US. A narrow window of opportunity exists for lung transplant in any patient who is sick enough to benefit from the operation, but healthy enough to survive months of waiting for a donor lung and then the subsequent surgery.

Upon reaching a critical condition, mechanical ventilation and extracorporeal membrane oxygenation (ECMO) are the only alternatives for respiratory support available to bridge acute and chronic respiratory patients to lung recovery or lung transplantation. Mechanical ventilation (MV) may maintain adequate gas exchange for short term support, but longer term support can lead to ventilator induced lung injury from barotrauma (high pressure), volutrauma (overdistension), and biotrauma (molecular and cell mediated inflammation), which can further worsen the respiratory status of the patient. ECMO is expensive and complicated, requiring the use of an external pump and blood circuit that have to be supervised continuously by highly trained technicians. The confinement of the patient in MV and especially ECMO leads to a progressive deconditioning that is reflected in higher postoperative complications and earlier mortality after transplant. Nevertheless, ECMO has been increasingly considered as the only alternative to bridge patients to lung transplant or lung recovery after an acute decompensation from their disease. More recently, with increasing experience at active transplant centers and improvement in ECMO technology, the concept of "ambulatory ECMO" has gained popularity and facilitates and expedites patient recovery after transplantation. Success in ambulatory ECMO underscores the importance of maintaining patient mobility. Currently available ambulatory ECMO systems combine existing blood pumps and bypass oxygenators into an integrated system but remain bulky and cumbersome and require frequent exchange of the oxygenators for longer term support.

Recent success with paracorporeal left ventricular assist devices (VADs) for heart failure patients has stimulated envisioning an ambulatory pump-lung device that can be a bridge to lung transplant or recovery. No fully integrated ambulatory pump-lungs are being used clinically, however. Many portable or ambulatory systems under development integrate a separate blood pump and oxygenator under a single controller unit but are cumbersome.

SUMMARY

In one aspect, a system for lung assist includes a plurality of fiber bundle sections. Each of the fiber bundle sections includes a fiber bundle housing defining a fiber bundle compartment therein and a fiber bundle positioned within the fiber bundle compartment. The fiber bundle includes a plurality of hollow gas permeable fibers adapted or configured to permit diffusion of gas between blood and an interior of the plurality of hollow gas permeable fibers. The plurality of hollow gas permeable fibers is positioned such that blood flows around the plurality of hollow gas permeable fibers when flowing through the fiber bundle compartment. The fiber bundle of each of the plurality of fiber bundle sections is different in at least one property from the fiber bundle of each of the other of the plurality of fiber bundle sections. Thus, each fiber bundle section is unique in at least one property of the associated fiber bundle. The fiber bundle housing further includes a gas inlet in fluid connection with the fiber bundle housing and in fluid connection with inlets of the plurality of hollow gas permeable fibers, a gas outlet in fluid connection with the housing and in fluid connection with outlets of the plurality of hollow gas permeable fibers, and a blood outlet in fluid connection with a first end of the fiber bundle. The fiber bundle housing also includes a first interface.

The system further includes a base section including a housing including a pressurizing compartment, a pressurizing mechanism within the pressurizing compartment, a blood inlet in fluid connection with the pressurizing compartment and a conduit in fluid connection with the pressurizing compartment at a first end thereof via which pressurized fluid exits the pressurizing compartment. The base further includes a second interface adapted to form a releasable, sealing connection with the first interface of one of the plurality of fiber bundle sections. A second end of the conduit is placed in fluid connection with a second end of the fiber bundle when the fiber bundle section is connected to the base section via the first interface and the second interface. The system may, for example, be a paracorporeal system.

In a number of embodiments, the pressurizing mechanism includes an impeller rotatable within the pressurizing compartment. In a number of embodiments, the housing of the base section includes a pressurizing section including the pressurizing compartment and an interface section. The interface section includes an extending section which extends from the pressurizing section and the second interface. The conduit may, for example, include a flow channel which extends through the extending section.

The plurality of hollow gas permeable fibers of each of the fiber bundles may, for example, extend generally perpendicular to the direction of bulk flow of blood through the fiber bundle from the second end of the fiber bundle to the first end of the fiber bundle. The plurality of hollow gas permeable fibers may, for example, include a plurality of layers of fiber fabric, wherein each of the plurality of layers of fiber fabric includes hollow gas permeable fibers. In a number of embodiments, adjacent layers of fiber fabric are rotated relative to each other such that the orientation of the plurality of hollow gas permeable fibers in adjacent layers of fiber fabric are of a different orientation.

In a number of embodiments, the plurality of hollow gas permeable fibers is formed in at least one generally cylindrical bundle. As described above, the generally cylindrical bundle may be formed from a plurality of layers of fiber fabric, wherein each of the plurality of layers of fiber fabric includes hollow gas permeable fibers. Once again, adjacent layers of fiber fabric may be rotated relative to each other such that the orientation of the plurality of hollow gas permeable fibers in adjacent layers of fiber fabric are of a different orientation.

In a number of embodiments, the flow channel is in fluid connection with a manifold formed in the extending section. The extending section may, for example, extend generally perpendicular to a plane of rotation of the impeller. The first interface of each of the fiber bundle sections may be, for example, attached to the second interface of the base section so that the axis of the fiber bundle of the one of the plurality of fiber bundle sections attached to the base section is oriented generally parallel to a plane of rotation of the impeller. The fiber bundle section attached to the base section may, for example, be positioned over the pressurizing compartment of the base section. Bulk flow of blood through the fiber bundle may, for example, be in a generally axial direction. In a number of embodiments, blood is blocked from flowing to the gas inlet and the gas outlet.

The plurality of fiber bundle sections may, for example, include fiber bundle sections of different lengths comprising fiber bundles of different lengths and thereby different fiber surface areas. At least one of the plurality of fiber bundle sections may, for example, be configured for use with pediatric patients, and at least one of the plurality of fiber bundle sections may, for example, be configured for use with adult patients.

In a number of embodiments, at least one combination of one of the plurality of fiber bundle sections and the base section is suitable for carbon dioxide removal in a first range of flow rates and is suitable for oxygenation and carbon dioxide removal in a second range of flow rates, wherein the second range of flow rates extends to higher flow rates.

In another aspect, a method of extracorporeal lung assist to a patient includes providing a plurality of fiber bundle sections. As described above, each of the fiber bundle sections includes a fiber bundle housing defining a fiber bundle compartment therein and a fiber bundle positioned within the fiber bundle compartment. The fiber bundle includes a plurality of hollow gas permeable fibers adapted or configured to permit diffusion of gas between blood and an interior of the plurality of hollow gas permeable fibers. The plurality of hollow gas permeable fibers is positioned such that blood flows around the plurality of hollow gas permeable fibers when flowing through the fiber bundle compartment. The fiber bundle of each of the plurality of fiber bundle sections is different in at least one property from the fiber bundle of each of the other of the plurality of fiber bundle sections. Thus, each fiber bundle section is unique in at least one property of the associated fiber bundle. The fiber bundle housing further includes a gas inlet in fluid connection with the fiber bundle housing and in fluid connection with inlets of the plurality of hollow gas permeable fibers, a gas outlet in fluid connection with the housing and in fluid connection with outlets of the plurality of hollow gas permeable fibers, and a blood outlet in fluid connection with a first end of the fiber bundle. The fiber bundle housing also includes a first interface. The method further includes providing a base section including a housing including a pressurizing compartment, a pressurizing mechanism within the pressurizing compartment, a blood inlet in fluid connection with the pressurizing compartment and a conduit in fluid connection with the pressurizing compartment at a first end thereof via which pressurized fluid exits the pressurizing compartment. The base further includes a second interface adapted to form a releasable, sealing connection with the first interface of one of the plurality of fiber bundle sections. A second end of the conduit is placed in fluid connection with a second end of the fiber bundle when the fiber bundle section is connected to the base section via the first interface and the second interface. The method also includes attaching one of the plurality of fiber bundle sections to the base section via connection of the first interface and the second interface, wherein the fiber bundle of the one of the fiber bundle sections is chosen for the patient. The fiber bundle section and the base section may be characterized as further described above.

As also described above, at least one combination of one of the plurality of fiber bundle sections and the base section may, for example, be suitable for carbon dioxide removal at in a first range of flow rates and is suitable for oxygenation and carbon dioxide removal in a second range of flow rates, wherein the second range of flow rates extends to higher flow rates.

In another aspect, a system for lung assist includes a fiber bundle section including a fiber bundle housing defining a fiber bundle compartment therein and a fiber bundle positioned within the fiber bundle compartment. The fiber bundle includes a plurality of hollow gas permeable fibers. The plurality of hollow gas permeable fibers may, for example, be adapted to or configured to permit diffusion of gas between blood and an interior of the plurality of hollow gas permeable fibers. The plurality of hollow gas permeable fibers is positioned such that blood flows around the plurality of hollow gas permeable fibers when flowing through the fiber bundle compartment. The fiber bundle housing further includes a gas inlet in fluid connection with the housing and in fluid connection with inlets of the plurality of hollow gas permeable fibers, a gas outlet in fluid connection with the housing and in fluid connection with outlets of the plurality of hollow gas permeable fibers, and a blood outlet in fluid connection with a first end of the fiber bundle. The fiber bundle section further includes a first interface. The system further includes a base section including a housing including a pressurizing compartment, a pressurizing mechanism within the pressurizing compartment, a blood inlet in fluid connection with the pressurizing compartment and a conduit in fluid connection with the pressurizing compartment at a first end thereof via which pressurized fluid exits the pressurizing compartment. The base section further includes a second interface adapted to form a releasable, sealing connection with the first interface of the fiber bundle section. A second end of the conduit is placed in fluid connection with a second end of the fiber bundle when the fiber bundle section is connected to the base section via the first interface and the second interface.

In still a further aspect, a method for providing lung assist includes selecting a fiber bundle section including a fiber bundle housing defining a fiber bundle compartment therein and a fiber bundle positioned within the fiber bundle compartment. As described above, the fiber bundle includes a plurality of hollow gas permeable fibers. The plurality of hollow gas permeable fibers is configured to or adapted to permit diffusion of gas between blood and an interior of the plurality of hollow gas permeable fibers. The plurality of hollow gas permeable fibers is positioned such that blood flows around the plurality of hollow gas permeable fibers when flowing through the fiber bundle compartment. The fiber bundle housing further includes a gas inlet in fluid connection with the housing and in fluid connection with inlets of the plurality of hollow gas permeable fibers, a gas outlet in fluid connection with the housing and in fluid connection with outlets of the plurality of hollow gas permeable fibers, a blood outlet in fluid connection with a first end of the fiber bundle. The fiber bundle section further includes a first interface. The method further includes releasably attaching the fiber bundle section to a base section including a housing including a pressurizing compartment, a pressurizing mechanism within the pressurizing compartment, a blood inlet in fluid connection with the pressurizing compartment and a conduit in fluid connection with the pressurizing compartment at a first end thereof via which pressurized fluid exits the pressurizing compartment. The base section further includes a second interface configured to or adapted to form a releasable, sealing connection with the first interface of the fiber bundle section. A second end of the conduit is placed in fluid connection with a second end of the fiber bundle when the fiber bundle section is attached to or connected to the base section via the first interface and the second interface.

The present devices, systems and methods, along with the attributes and attendant advantages thereof, will best be appreciated and understood in view of the following detailed description taken in conjunction with the accompanying drawings.

BRIEF DESCRIPTION OF THE DRAWINGS

FIG. 1A illustrates a perspective view of an embodiment of an extracorporeal assist lung or paracorporeal ambulatory assist lung apparatus, device or system hereof in which a smaller fiber bundle section is placed in connection with the base section of the device.

FIG. 1B illustrates a perspective view of the paracorporeal ambulatory assist lung device of FIG. 1A, in which the smaller fiber bundle section illustrated in FIG. 1A has been removed and a larger fiber bundle section has been placed in connection with the base section of the device.

FIG. 3A illustrates a front view of the paracorporeal ambulatory assist lung device of FIG. 1A with the smaller fiber bundle section in connection with the base section.

FIG. 3B illustrates a section A-A (with reference to FIG. 3A) cross-sectional view of the system of FIG. 1A with the smaller fiber bundle section in connection with the base section.

FIG. 3C illustrates a section B-B (with reference to FIG. 3A) cross-sectional view of the system of FIG. 1A with the smaller fiber bundle section in connection with the base section.

FIG. 4B illustrates a side view of the paracorporeal ambulatory assist lung device of FIG. 1A with the larger fiber bundle connected to the base section.

FIG. 4C illustrates a rear view of the paracorporeal ambulatory assist lung device of FIG. 1A with a rear panel removed to illustrates the flow path channel from the pressurizing section into a manifold in fluid connection with the fiber bundle section.

FIG. 4D illustrates a side view of the paracorporeal ambulatory assist lung device hereof similar to the device of FIG. 1A with a larger fiber bundle connected to the base section.

FIG. 4E illustrates a rear view of the paracorporeal ambulatory assist lung device of FIG. 4D with a rear panel removed to illustrates the flow path channel from the pressurizing section into a manifold in fluid connection with the fiber bundle section.

DETAILED DESCRIPTION

Figure 2A:
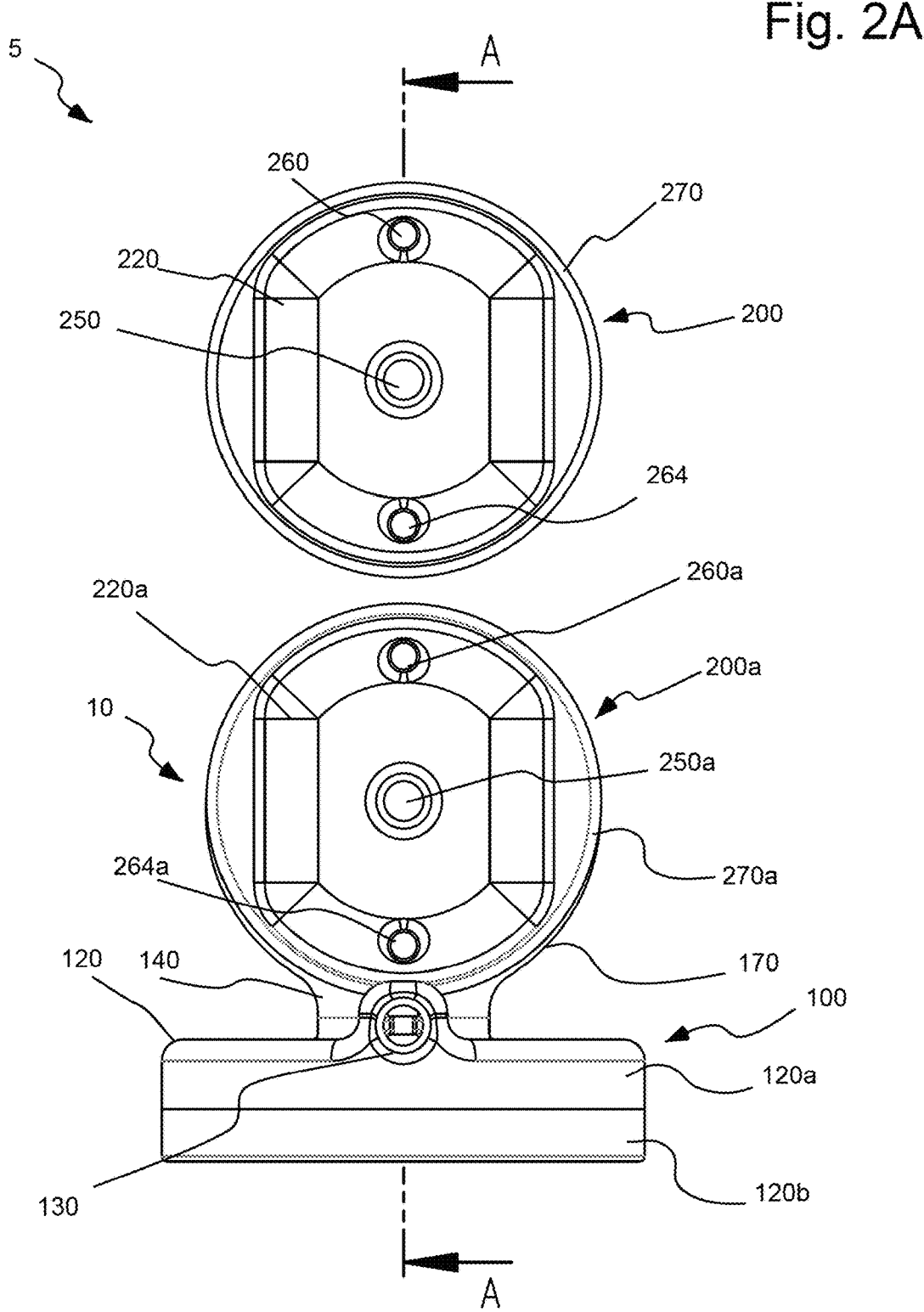
FIG. 2A illustrates a front view of the paracorporeal ambulatory assist lung device of FIG. 1A with the larger fiber bundle section in position for attachment to the base section of the device and the smaller fiber bundle section positioned above the larger fiber bundle section.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "an impeller" includes a plurality of such impellers and equivalents thereof known to those skilled in the art, and so forth, and reference to "the impeller" is a reference to one or more such impellers and equivalents thereof known to those skilled in the art, and so forth. Recitation of ranges of values herein are merely intended to serve as a shorthand method of referring individually to each separate value falling within the range. Unless otherwise indicated herein, each separate value and intermediate ranges are incorporated into the specification as if individually recited herein. All methods described herein can be performed in any suitable order unless otherwise indicated herein otherwise clearly contraindicated by the text.

As used herein in reference to device 10, the terms "axial", "axially" or like terms refer generally to an axis around which a component (for example, fiber bundle 300 or impeller 400) of device 10 is formed (although not necessarily symmetrically therearound). The term "radial" refers generally to a direction normal to such an axis. The terms "rear", "rearward" or like terms refer generally to a direction along axis x of FIG. 1A away from or opposite the gas and fluid ports of device 10. The terms "front", "forward" or like terms refer generally to a direction along axis x toward the gas and fluid ports of device 10. The terms "up", "upward" or like terms refer generally to a direction along axis y of FIG. 1A toward fiber bundle section 200 and away from pressurizing section 122 of base section 100, while the terms "down", "downward" or like terms refer to a direction along axis y away from fiber bundle section 200 and toward pressurizing section 122 of base section 100. The terms "side", "sideways" or like terms refer to a direction orthogonal to an up or down direction and orthogonal to an axial direction as described above. In general, terms related to direction and/or orientation as set forth herein are used to describe relative positions of the elements of the described embodiment and are not limiting unless otherwise indicated herein or otherwise clear from the text hereof.

In a number of embodiments, extracorporeal/paracorporeal ambulatory assist lung system hereof provide advantages in gas transfer efficiency and biocompatibility. The systems hereof may, for example, be designed for either central and/or peripheral cannulation and respiratory support of, for example, 1-3 months duration before device change-out may be required. Systems hereof are, for example, amenable to patients suffering from severe acute respiratory failure (ARDS) to chronic patients suffering from COPD or severe pulmonary hypertension (PH). Paracorporeal apparatuses, devices or systems are extracorporeal devices/systems generally located immediately adjacent to the body during use. In other words, paracorporeal devices or systems are "wearable" or ambulatory devices or systems. The apparatuses, devices and systems hereof are well suited for paracorporeal/ambulatory use as well as use as generally stationary extracorporeal use.

In many ambulatory devices or system under development, a blood pump is connected by one or more conduits (for example, lengths of tubing) to an oxygenator. While a number of systems have integrated blood pumps, the blood leaving the impeller unit of such devices typically travels through channels before being distributed by manifolds into the hollow fiber bundle compartment. Recently, devices which are less cumbersome than many other devices under development while providing for increased ambulatory respiratory assist were disclosed in PCT International Patent Application Publication No. 2016/210089, the disclosure of which is incorporated herein by reference. Such devices provide a highly integrated blood pump and lung, in which a pump mechanism such as an impeller pressurizes blood for flow through hollow gas permeable fibers (sometimes referred to herein as a fiber bundle). Such devices may, for example, be designed to be worn in a holster or vest paracorporeally. Moreover, such devices may, for example, provide for increased average or mean velocity through the fiber bundle as compared to other devices, which enhances gas exchange. The integrally formed extracorporeal systems for lung assist of PCT International Patent Application Publication No. 2016/210089 include an integrated housing having a blood flow inlet in fluid connection with a fiber bundle compartment and a pressurizing stator compartment.

In a number of embodiments as illustrated in FIGS. 1A through 4, device 10 includes a first, base or blood pressurizing section 100 (hereinafter referred to as base section 100) and a modular or releasably connectible second, fiber bundle or gas exchange section 200 (hereinafter referred to as fiber bundle section 200, 200a etc.). In a number of embodiments, base section 100 and fiber bundle section 200 are releasably connectible so that a pressurizing system and the fiber bundle are encompassed within a relatively small form factor. As further described below, fiber bundle section 200 may be readily removed and replaced with another fiber bundle section such as fiber bundle section 200a of FIG. 1B to provide a fiber bundle of, for example, a different size, a different configuration, a different surface treatment, a different fiber composition, etc. Device 10 may thereby provide for efficient and significant gas transfer rate in a number of different uses or treatments without inducing significant blood damage. Moreover, fiber bundle section such as fiber bundle section 200 or 200a may be readily replaced with another like or identical fiber bundles section 200 or 200a, respectively, in the case of, for example, damage, contamination or wear.

Figure 2B:
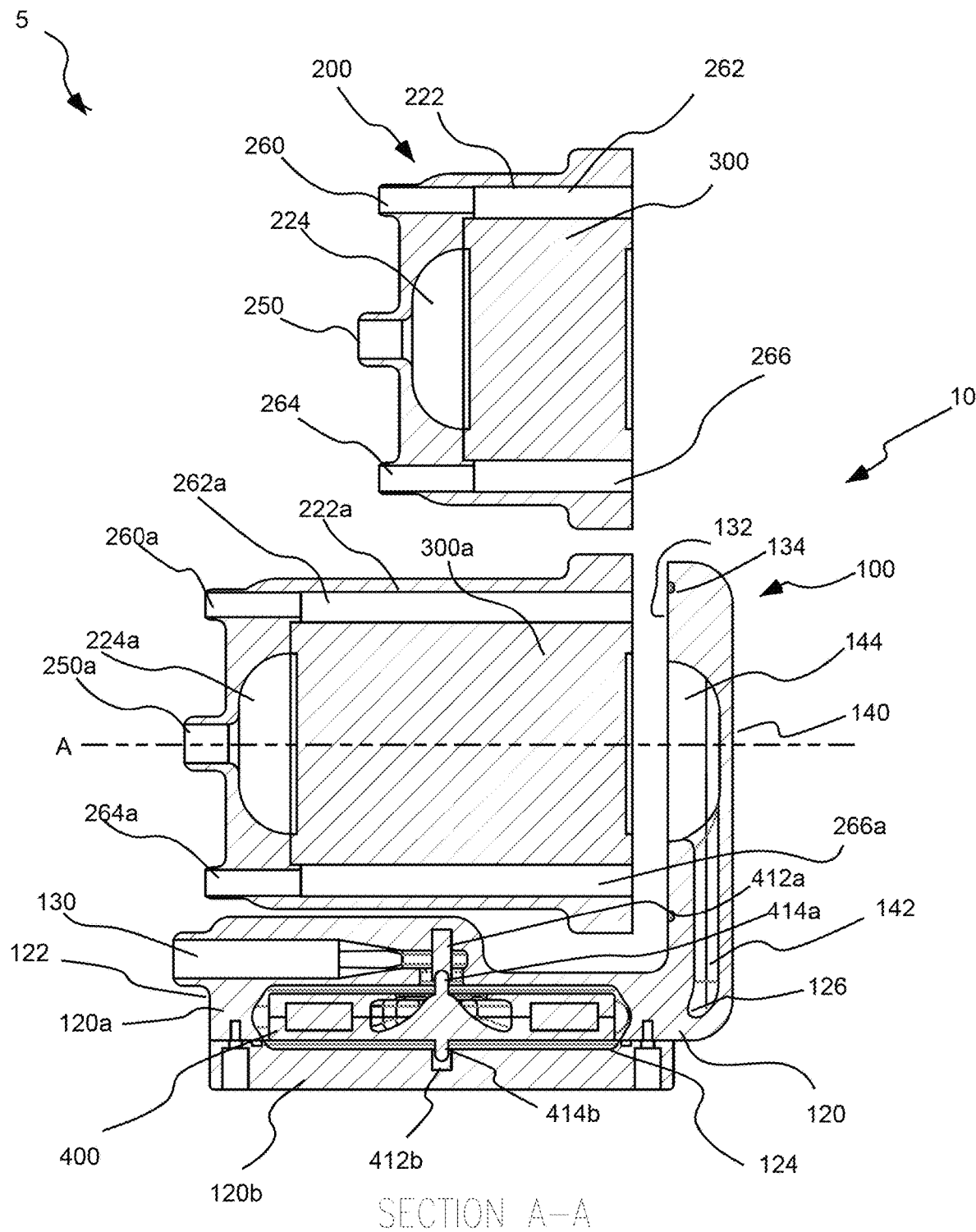
FIG. 2B illustrates a side cross-sectional view of the paracorporeal ambulatory assist lung device of FIG. 1A with the larger fiber bundle section in position for attachment to the base section of the device and the smaller fiber bundle section positioned above the larger fiber bundle section.

Fiber bundle section 200 includes a housing 220 which includes a fiber bundle compartment 222 as, for example, illustrated in, for example, FIGS. 2B and 3B. Fiber bundle compartment 222 houses a fiber bundle 300 and provides a gas pathway designed to uniformly perfuse the gas side of fiber bundle 300 with a sweep gas which may be oxygen or a gas mixture including oxygen.

As, for example, illustrated in the embodiments of FIGS. 2A and 2B, systems 5 hereof may include a base section 100 and a plurality of different fiber bundle sections 200, 200a etc. Two fiber bundle sections 200 and 200a are illustrated in FIGS. 2A and 2B, but more fiber bundle sections may be provided. In a number of embodiments, fiber bundle sections 200 and 200a (and other fiber bundle sections hereof) are formed to have generally identically dimensions other than the length thereof. Elements of fiber bundle section 200a are numbered similarly to corresponding elements of fiber bundle section 200 with the addition of the designation "a" thereto. Fiber bundle 300a may, for example, be formed to have dimensions generally identically to fiber bundle 300 other than the length thereof. Upon formation, the gas exchanging portion of fiber bundle 300 (excluding any potting) had a diameter of 1.75 inches (0.044 meters) and a length of 1.52 inches (0.039 meters). Fiber bundle 300a had a diameter of 1.75 inches (0.044 meters) and a length of 3.20 inches (0.081 meters). In a number of embodiments, fiber bundle 300 had an overall surface area for gas exchange or total fiber surface area of 0.3 m$^2$. Fiber bundle 300 included 96 PMP fiber layers. Fiber bundle 300a had an overall surface area for gas exchange or total fiber surface area of 0.65 m$^2$. Fiber bundle 300a included 200 PMP fiber layers.

In the embodiments of Figures IA through 4E, numerous fiber bundle/device properties can be changed by switching between fiber bundle sections including, but not limited to, fiber bundle length (and, thereby, overall surface area for gas exchange), fiber bundle composition (for example, fiber bundle material, surface treatment), etc. The fiber bundle properties can vary over a wide range to be specifically adapted for a particular use or function, for a particular patient group, or even for a particular patient.

In the illustrated embodiment of FIGS. 1 through 4E, fiber bundle section 200 and associated fiber bundle 300 were, for example, designed for pediatric use, while fiber bundle section 200a and associated fiber bundle 300a were designed for adult use. In the case of each of fiber bundle sections 200 and 200a, device 10 may, for example, be used for oxygenation and/or carbon dioxide removal. The integrated pump, including impeller 400 (a closed or enclosed impeller in a number of embodiments), draws venous blood from a patient via an inflow cannula (see FIG. 3B) placed within a blood vessel. Blood is pumped through the gas-exchanging fiber bundle, which is operable to transfer oxygen to and remove carbon dioxide from the blood. After the blood passes through the fiber bundle, the blood is returned to the patient's circulatory system via an outflow cannula (see FIG. 3B). The required levels of blood flow, pumping, and gas exchange provided by device 10 during respiratory support depends upon patient size (for example, a pediatric patient or an adult patient) as well as the nature of the respiratory insufficiency. In the case wherein carbon dioxide removal rather than oxygenation is the primary goal, lower blood flow rates and less invasive cannulation strategies may be used. When carbon dioxide is the primary goal, the methodology is typically referred to as extracorporeal carbon dioxide removal or $ECCO_2R$.

In a number of embodiments, all gas and fluid inlets and outlets (collectively ports) are oriented in generally the same directions upon assembly of device 10 by connecting a fiber bundle section hereof to base section 100 (see, for example, Figures IA through 2B). In the illustrated embodiment, the axes of gas inlet 260, gas outlet 264, fluid inlet 130 and fluid outlet 250 are generally parallel (for example, within less than 20, 10 or even 5 degrees of being parallel). In the embodiment of FIGS. 1 through 4C, the inlets and outlets are positioned on a forward or front side of device 10. In the illustrated embodiment, such axes are generally coplanar (for example, within less than 20, 10 or even 5 degrees of being coplanar). By orientating all gas and fluid ports in generally the same direction, connection of tubing to such ports and wearing of device 10 hereof with attached tubing is facilitated. As set forth above, orientating all gas and fluid ports in generally the same direction indicates that the axes of each of the ports is within 20°, 10°, 5° or less of being colinear with all other axes.

In a number of embodiments, the dimensions of device 10 were no more than 13.2 cm (5.2 inches) in height (the y dimension in FIG. 1A), no more than 11.4 cm (4.5 inches) in width (the z dimension in FIG. 1A), and no more than 14 cm (5.5 inches) in length (the x dimension in FIG. 1A). In a number of embodiments, the length of fiber bundle section varied between 6.9 cm (2.7 inches) and 11.2 cm (4.4 inches). The weight of device 10 with fiber bundle section 200 may, for example, be no greater than 550 g, or no greater than 500 g, while the weight of device 10 with fiber bundle section 200a may be no greater than 620 g or nor greater than 570 g. In a number of embodiments, the priming volume of device 10 with fiber bundle section 200 was approximately 125 ml, and the priming volume of device 10 with fiber bundle section 200a was approximately 160 ml. The form factor of device hereof may be further reduced by increasing pumping efficiency (for example, by further optimizing impeller design).

In that regard, a pressurizing mechanism such as a rotating element or an impeller 400 may be positioned within a pressurizing or pumping (impeller/stator) compartment 124 a housing 120 of base section 100. In the illustrated embodiment, base section 100 includes a first or pressurizing section 122 which houses pumping or pressurizing compartment 124 and a second, or interface section 140 which extends at an angle from first section 122 to form an interface for connection with a fiber bundle section hereof. In the illustrated embodiment, extending section 140 extends at an angle of approximately 90° to the plane of rotation of impeller 400 as defined by pumping or pressurizing compartment 124 of first section 122. Pumping or pressurizing compartment 124 was formed as an impeller stator/volute compartment of first section 122. In the illustrated embodiment, first section 122 and pumping or pressurizing compartment 124 thereof were formed via connection of a first or upper housing section or portion 120*a* and a lower or second housing section 120*b* of base housing 120. Lower or second housing section 120*b* of base housing 120 (see, for example, FIG. 4A) was sized to allow insertion of impeller 400 into impeller stator/volute compartment 124 of base housing 120. Pumping or pressurizing compartment 124 houses impeller 400 and may be designed in accordance with traditional pump theory to maximize the pumping efficiency of impeller 400. Impeller 400 rotates within pumping or pressurizing compartment 124 of housing 120.

Fiber bundle section housing 220 and base section housing 120 are formed from rigid materials. In general, such rigid materials do not deform or flex significantly under the conditions of use. In a number of embodiments, fiber bundle section housing 220 and base section housing 120 are formed from polymeric materials and, typically, from the same polymeric material. The housing sections may, for example, be formed from extrusion.

The stator section of a centrifugal pump, after flow exits the impeller, is usually either a diffuser or a volute. The purpose of each of these two stator types is to efficiently diffuse velocity energy into pressure. Diffusers are characterized by a plurality of radially symmetric diffusing passageways surrounding the impeller. Either a volute-shaped or annular collector is used in tandem with the diffuser. Volutes are characterized by one or more scroll-shaped diffusing passageways (one in a number of embodiments hereof), depending on the pump configuration. A volute hereof receives fluid being pumped by the impeller, slowing down the fluid's flow rate and converting kinetic energy into pressure. The volute curves and increases in area as it approaches the discharge port.

Impeller 400 may, for example, be partially magnetically supported via one or more magnets positioned on or within impeller 400. Impeller 400, in the illustrated embodiment, is positioned within impeller volute compartment 124 such that the net hydrodynamic load on impeller 400 is upwards (in the orientation of the Figures). Thus, magnets used to support impeller 400 may exert a downward force on impeller 400. As, for example, discussed in PCT International Publication No. WO2014/085620, one or more magnets may be seated in one or more seating of impeller 400 and (in cooperation with another magnet which may be within or external to impeller volute compartment 124) is operable to apply force offset the combined hydrodynamic and coupling magnet forces, thereby minimizing the axial forces applied to the bearings, and improving overall system durability. Top and bottom pivot bearings 412*a* and 412*b* (see FIG. 4A), respectively, may, for example, be ultra-high-molecular-weight polyethylene (UHMWPE) pivot and cup type bearings housed in a stainless steel shell, which maximizes their resistance to wear.

Figure 2C:
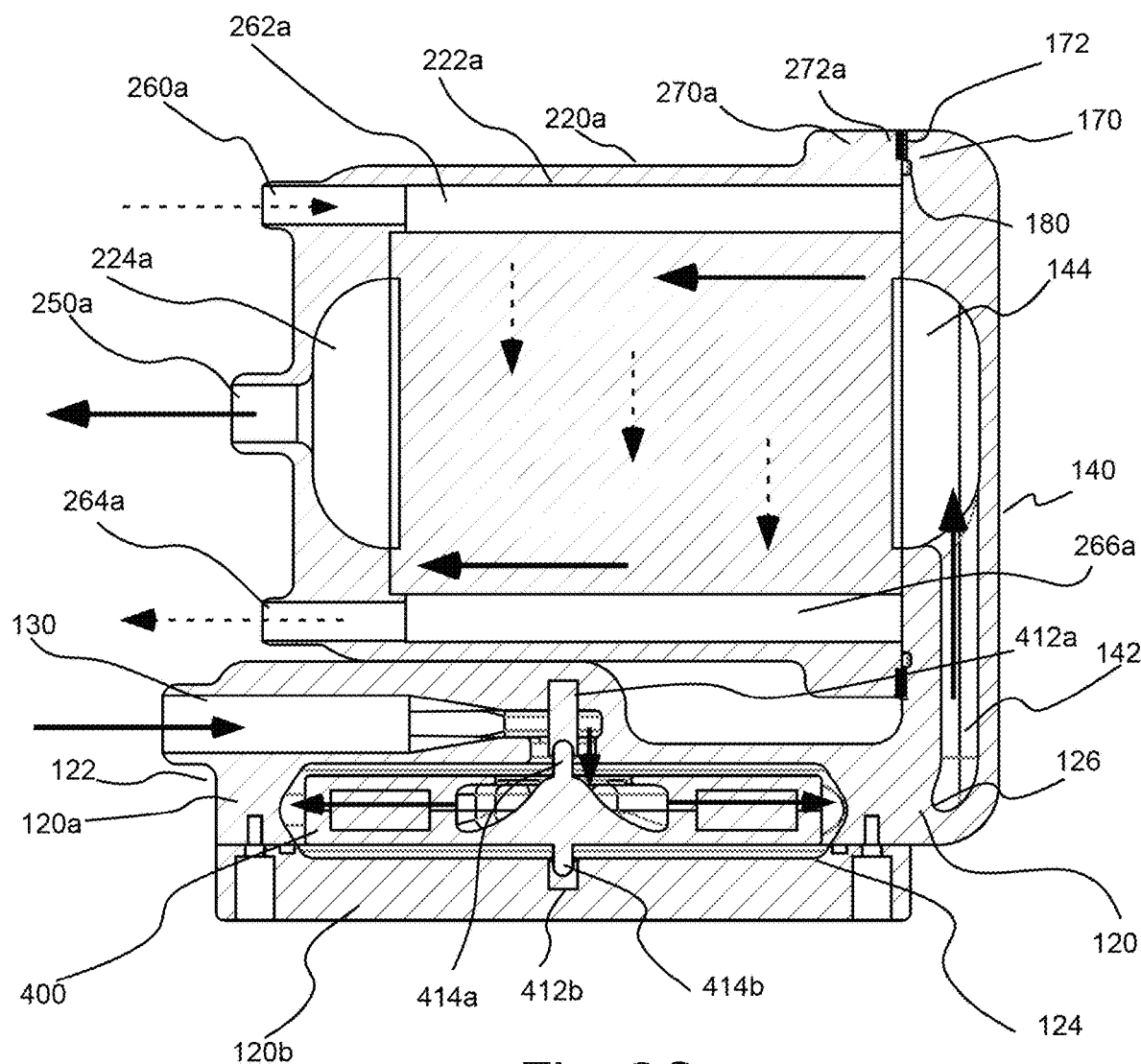
FIG. 2C illustrates a side cross-section view of the paracorporeal ambulatory assist lung device of FIG. 1A with the larger fiber bundle connected to the base section and in which solid arrows indicate blood flow through the device and dashed arrows indicate gas flow through the device.
Figure 2D:
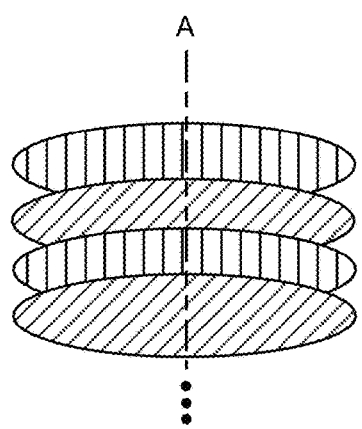
FIG. 2D illustrates a perspective, exploded view of various layers of an embodiment of a fiber bundle hereof wherein the orientation of the fibers in adjacent layers is rotated with respect to each other (wherein the fibers within individual layers are oriented in generally the same direction).
Figure 5A:
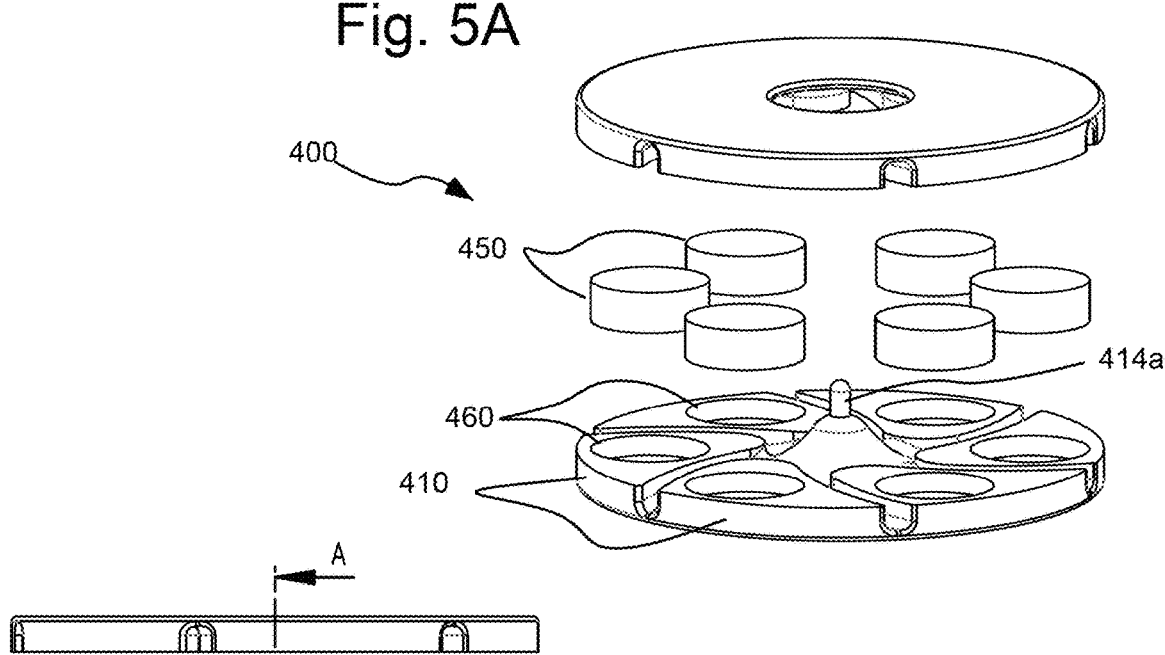
FIG. 5A illustrates a perspective, disassembled or exploded view of the impeller of the device of FIG. 1A.

FIG. 2C illustrates fluid (blood) flow (solid arrows) and sweep gas flow (dashed arrows) through device 10. In that regard, a fluid such as blood is drawn into the central portion of impeller 400 via a fluid inlet 130 formed in base section 100 and centrifugally spun outwards via impeller vanes 410 (see, for example, FIGS. 3C and 5A) as indicated by the radially outward oriented solid arrows in FIG. 2C. Blood is then channeled to fiber bundle 300 as shown in, for example, FIGS. 1B and 3C. As, for example, illustrated in FIG. 3C, a channel 126 extends from impeller volute compartment 124 to a flow channel 142. At the point that channel 126 extends from impeller volute compartment 124, flow channel 142 may, for example, extend the height (that is, the vertical dimension in the orientation of FIG. 2C) of impeller 400 to, for example, maximize washing on the underside of impeller 400, as this is a common area for thrombus deposition in pivot pumps. In the illustrated embodiment, channel 126 extends generally tangentially (for example, within 5 degrees of tangentially therefrom) from impeller volute compartment to connect to flow channel 142. In a number of embodiments, flow channel 142 had a circular cross-section. Channel 126 extends rearward at an angle to approximately a centerline of impeller 400 where channel 126 connects to flow channel 142.

Flow Channel 142 may be incorporated into base housing 120 (that is, within extending section 140) in a manner that it does not further increase the form factor of fiber bundle 300 and, thereby, fiber bundle section 200. In the illustrated embodiment (see, for example, FIGS. 2B, 2C and 4C), flow channel 142 travels vertically upward (in the orientation of the drawings) and at an angle of approximately 90° (that is approximately perpendicularly or perpendicularly) to the plane of rotation of impeller 400 through extending section 140 of base section 100 and enters a fluid/blood inlet volume or manifold 144 portion formed in a forward-facing portion of extending section 140 where the fluid/blood contacts a second or rearward surface of fiber bundle 300. Providing rounded or arced corners/ends in flow channel 142 may assist in, for example, reducing or minimizing hemolysis and thrombosis. In a number of embodiments, flow channel 142 has a round or circular cross-sectional shape.

In a number of embodiments, the blood enters the second or rearward end of fiber bundle 300 from manifold 144 and passes around the hollow fibers thereof. After passing through fiber bundle 300, blood exits system 10 via an outlet volume or manifold 224, which is in fluid connection with a first or forward end of fiber bundle 300 at a first end thereof and with a blood/fluid outlet 250 at a second end thereof. The liquid/fluid flow path may be separated from the gas flow path through device 10 by abutment/sealing between (i) the periphery of the rear face of fiber bundle 300 and surface 146 and (ii) the periphery of the front face of fiber bundle 300 and fiber bundle housing 220.

In the illustrated embodiment, fiber bundle section 200 includes an interface 270 (a fiber bundle section 200*a* includes a like interface 270*a*) which connects to a cooperating interface 170 of extending section 140 of base section 100. Each fiber bundle section hereof may include a like or identical interface which cooperates with interface 170 to form a sealed connection between one of the fiber bundle sections hereof and base section 100. Fiber bundle sections hereof are thus each readily connectible to and removable from base section 100 hereof for devices 10 of differing flow and/or mass exchange properties (as well as differing dimensions, volume and/or weight). As illustrated schematically in the representative embodiment of FIG. 2C, fiber bundle section 200a may include an interface 270a having a connector 272a which cooperates with a cooperating connector 172 on interface 170 to form a sealed connection between interface 270a of fiber bundle section 200a and interface 170 of base section 100. Other fiber bundle sections hereof may similarly include like connectors to cooperate with cooperating connector 172. Connector 272a (and like or identical connectors of other fiber bundle sections hereof) may cooperate with cooperating connector 172 via sliding fits, snap fits, threaded fits, Luer lock connection fits etc. as known in the mechanical/medical connection arts. A sealing connection between interface 270a and interface 170 may, for example, be facilitated by a seal 180 such as an O-ring, which is seated in a seating formed in forward surface 146 of the illustrated embodiment.

The gas pathway in device 10 may, for example, be relatively simple. Gas flows in through a gas inlet port 260 into a channel 262 on one side of fiber bundle 300 and out through a gas outlet port 264 in fluid connection with a channel 266 on the other side of fiber bundle 300. Thus, gas flow through fiber bundle 300 is in the average or bulk direction of the dashed arrows in FIG. 2C. Channel 262 is the inlet to the gas pathway and channel 266 is the outlet. The sweep gas passes through 262 across (that is radially across) the lumens of the fibers into channel 266. Channel 262 is sealed from channel 266, for example, by sealing contact between an inner surface of housing 220 and fiber bundle 300 or by sealing contact with a sealing member which extends between an inner surface of housing 220 and fiber bundle 300. In a number of embodiments, the height of channels 262 and 266 were approximately 0.8 cm (0.3 inches). The width may, for example, be chosen to assist in uniformly perfusing all of the fibers in fiber bundle 300. The direction of gas flow may, for example, be such that it is generally along or assisted by the direction of gravity when device 10 is worn by the patient, so that any condensation that is built up will be cleared as a result of the effect of gravity.

Figure 4A:
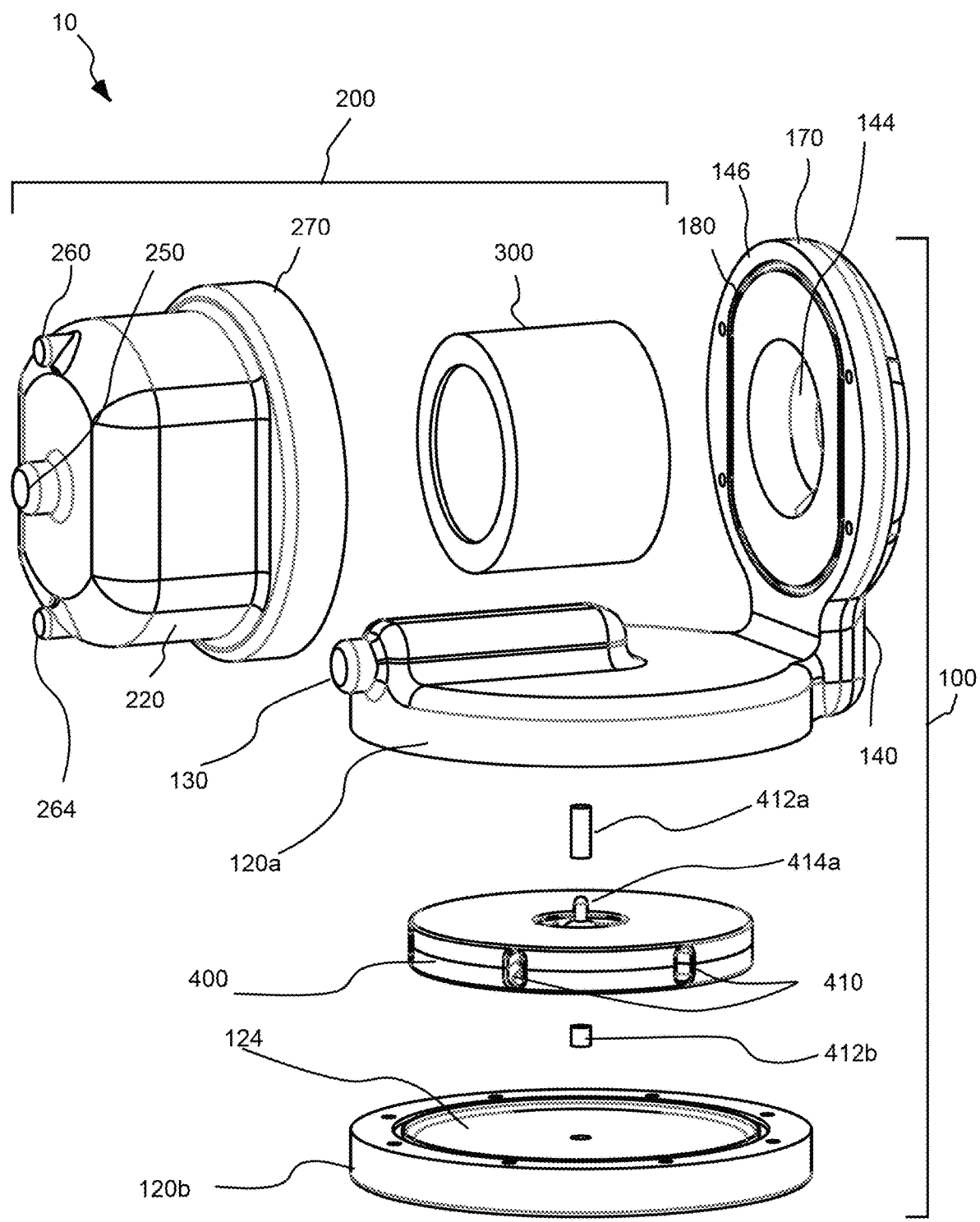
FIG. 4A illustrates a perspective, disassembled or exploded view of the paracorporeal ambulatory assist lung device of FIG. 1A, including the smaller fiber bundle section.

FIG. 4A illustrates a perspective, disassembled or exploded view of device 10 including smaller, pediatric fiber bundle section 200. FIG. 4B illustrates a side view of device 10 with larger, adult fiber bundle 200a connected to base section 100. FIG. 4C illustrates a rear view of device 10 with a rear panel removed to illustrate channel 142 extending from the pressurizing section 122 to manifold 144 (through extending section 140). As described above, in the illustrated embodiment, channel 142 is incorporated into base housing 120 within extending section 140 in a manner that it does not further increase the form factor of fiber bundle 300 and, thereby, fiber bundle section 200. As described above, channel 142 travels in a plane that is orthogonal to or perpendicular to the plane of rotation of impeller 400 through extending section 140 of base section 100 and enters a fluid/blood inlet volume or manifold 144 portion.

FIG. 4D illustrates a side view of another embodiment of paracorporeal ambulatory assist lung device 10' hereof that is similar in design and operation to device 10 with larger, adult fiber bundle section 200a connected to base section 100'. In describing device 10', elements of device 10' include reference numbers similar to corresponding elements of device 10 with the addition of the designation "'". FIG. 4E illustrates a rear view of device 10' with a rear panel removed to illustrate flow path channel 142' which extends from pressurizing section 122' into a manifold 144'. Similar to flow channel 142 of device 10, flow channel 142' extends upward from pressurizing section 122', through extending section 140, in a plane generally perpendicular to the plane of rotation of impeller 400'. However, flow channel 142' does not extend generally linearly and vertically upward through extending section 140', but travels in a curvilinear path through extending section 140' to manifold 144'. Once again, providing rounded or arced corners/ends in flow channel 142' may assist in, for example, reducing or minimizing hemolysis and thrombosis. In a number of embodiments, flow channel 142' may, for example, have a round or circular cross-sectional shape. As seen in a comparison of FIGS. 4E and 4C, the from factor of extending section 140' is larger than that of extending section 140, resulting in device 10' having a slightly larger form factor and being a slightly heavier than device 10'. The path or shape of flow channels such as channels 142 and 142' may, for example, be readily optimized based upon variables such as impeller design, pressure requirements, hemolysis limits, device form factor, etc. using known engineering principles.

Similar to device 10, all gas and fluid inlets and outlets (collectively ports) maybe oriented in generally the same direction upon assembly of device 10'. In the illustrated embodiment, the axes of gas inlet 260', gas outlet 264', fluid inlet 130' and fluid outlet 250' are generally parallel and positioned on one side of device 10'. As described above, by orientating all gas and fluid ports in generally the same direction, connection of tubing to such ports and wearing of device 10' hereof with attached tubing is facilitated.

Fiber bundle 300 may, for example, be manufactured in accordance with methods described in PCT International Publication No. WO2014/085620, the disclosure of which is incorporated herein by reference. In a number of embodiments, fiber bundle 300 was a generally cylindrical bundle of hollow fiber membranes (for example, fiber arrays, membranes or fabrics as described above) stacked in layers at, for example, 5-15 degree angles to one another and aligned generally perpendicular to the principal direction of blood flow (that is, generally perpendicular to axis A of fiber bundle 300—see FIGS. 2B and 2D)) to maximize gas exchange. In a number of representative embodiments studied herein, fiber bundle 300 was a generally cylindrical bundle of hollow fiber membranes stacked in layers at approximately 14 degree angles to one another. In that regard, the fibers were cut into round sheets and stacked at a 14 degree angle between adjacent sheets into a potting mold. The ends of the hollow fibers were potted into semi-circular gas manifold channels (gas inlet manifold channel 262 and gas outlet manifold channel 266). Polyurethane glue was injected into the mold by using centrifugal force generated by spinning the mold in a lathe. The polyurethane binds all the fibers into fiber bundle 300. The thickness of the potting glue was roughly 0.25 in and was chosen to provide adequate mechanical support.

Aligning the hollow fibers generally perpendicular (for example, within no more 5 degrees from perpendicular or even within nor more than 2.5 degrees of perpendicular) to axis A can significantly decrease volume (that is, improve compactness) as compared to systems in which hollow fibers are generally parallel to the axis of the housing/blood flow.

In a number of embodiments, fiber bundle 300 was sealed to axially extending sealing sections formed on an inner wall of fiber bundle compartment 222 to form generally semi-circular (in cross-section) manifolds. The sealing sections may, for example, extend radially inward to contact and form a sealing connection with fiber bundle 300. Two sealing section may be used to form generally semi-circular (that is, extending approximately 180 degrees) manifolds. Additional sealing sections may, for example, be used to create manifolds that extend around the inner circumference of fiber bundle compartment 222 less than 180 degrees.

Fiber bundle 300 may, for example, be wound and positioned within a four-piece reusable mold made from, for example, acetal (Delrin) for potting. During potting, two-part polyurethane adhesive (available from Cas Chem, of Bayonne, NJ) is injected into the mold. The mold is then centrifuged to assure even distribution around the periphery without any voids. Once the adhesive has cured, the potted fibers are removed and trimmed. This procedure establishes a common gas pathway between all fibers.

As described above, the fibers used in the studies of devices 10 were provided in array, fabric or membrane form. Approaches to improving thromboresistance include the use of zwitterionic molecular species attached (for example, covalently) to the surface of the fibers without significantly affecting gas transport across the fiber surface. Carbonic anhydrase may, for example, be immobilized on or in the vicinity of fiber surfaces to enhance carbon dioxide removal. See, for example, U.S. Pat. No. 7,763,097, the disclosure of which is incorporated herein by reference. Furthermore, blood flow paths and patterns in device 10 may be optimized using for example computational fluid dynamics or CFD for improved hemocompatibility. The ultimate anticoagulation requirements for device 10 may also be further reduced because blood exiting device 10 flows through the patient's lungs, which can continue to act as a filter of small emboli.

As described above, blood enters device 10 through fluid flow inlet or blood flow inlet port 130 and is pumped by impeller 400. In a number of studied embodiments, impeller 400 was supported by two pivot bearings 412a and 412b mounted into housing 120 and aligned with and cooperate with extending members 414a and 414b on the central axis of radial impeller 400. As known in the bearing arts, extending member 414a and 414b may, for example, include a rounded end that is rotatable relative to a bearing cup of bearings 412a and 412b (for example, similar to a ball and socket joint). The bearing cups may, for example, be formed from ultrahigh molecular weights polyethylene and are available, for example, from Modern Plastics of Shelton, Connecticut. The use of pivot bearings 412a and 412b eliminates the need for seals and bearings. The pivot bearings maintain impeller 400 axially and radially aligned within system 10. Also, secondary saline infusion used in some systems to keep blood from contacting friction/heat generating components are not required. Fresh blood enters device 10 and flows across the pivot bearings, flushing the area with fresh fluid.

Figure 5B:
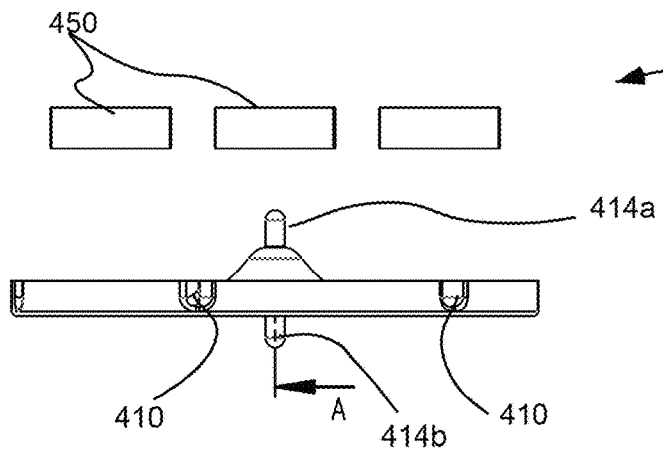
FIG. 5B illustrates a side, disassembled or exploded view of the impeller of the device of FIG. 1A.
Figure 5C:
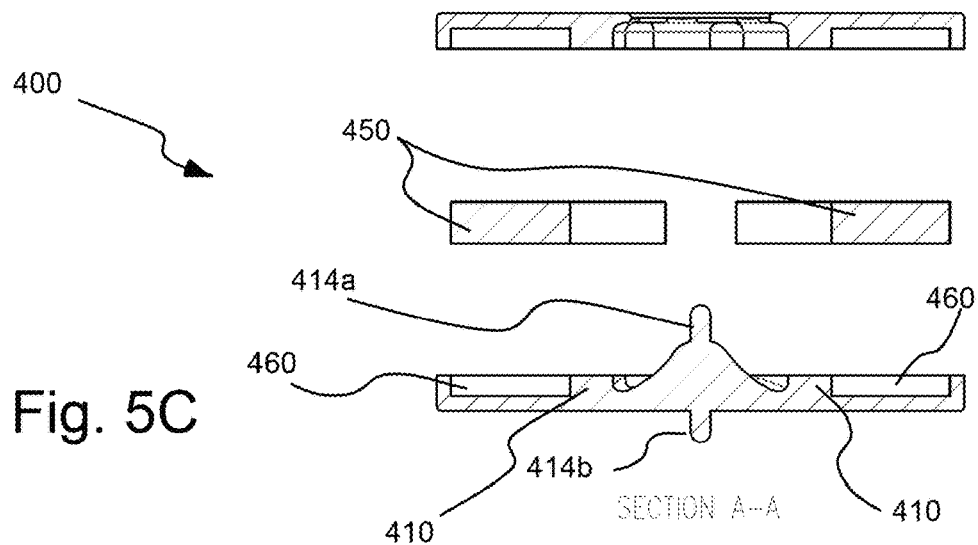
FIG. 5C illustrates a section A-A (see FIG. 5B) cross-sectional, disassembled or exploded view of the impeller of the device of FIG. 1A.

Magnetically suspended or levitated impellers without bearings may, for example, be used to further increase longevity. However, device 10, in a number of embodiments, may require periodic change-out (for example, every 1-3 months) as a result of fouling in the lung compartment. A simpler and less complex approach of magnetic coupling of impeller 400, but not magnetic levitation, was chosen in a number of embodiments. In the illustrated embodiment, magnets 450, which are seated in seatings 460 (see FIG. 5A-5C) on rotating impeller 400 couple magnetically to rotating magnets on an external motor drive (shown schematically in FIG. 2A) to maintain a hermetic seal. System 10 may, for example, be powered by a power module (see FIG. 2A) including one or more batteries. In the illustrated embodiment, six relatively small (0.75" diameter by 0.25" thick) magnets 450 are used as "coupling magnets" to maintain a magnetic couple between the motor drive and impeller 400. One or more magnets may also be used to stabilize the hydrodynamic force.

Operation of device 10 is further discussed below for device 10 including fiber bundle section 200. However, operation with other fiber bundle sections hereof will be essentially the same. During operation, an oxygen-containing "sweep gas" (for example, oxygen) flows into gas inlet channel 262 via gas flow inlet 260 and is distributed through the lumens of the individual fiber membranes of fiber bundle 300. Oxygen ($O_2$) diffuses out of the fibers into the flowing blood (flowing around the fibers and generally perpendicular to the orientation thereof) as carbon dioxide ($CO_2$) diffuses from blood into the fibers and is carried by the sweep gas to outlet channel 266 and therethrough to gas flow outlet 264. As described above, the blood then leaves device 10 via blood flow outlet 250. Oxygen and carbon dioxide exit the lumens of the fibers into gas outlet channel 266. As, for example, illustrated in FIG. 3B, the ends of fiber bundle 300 contacts a first end of fiber bundle compartment 222 of fiber bundle section housing 220 and form gas inlet channel 262 and gas outlet channel 266. Blood is thereby prevented from directly flowing into gas inlet channel 262 and/or gas outlet channel 266. The potting of fiber bundle 300 prevents blood from flowing radially out of fiber bundle 300 and into gas inlet channel 262 and/or gas outlet channel 266.

Devices 10 used in studies hereof were not fully optimized. Further optimization may be effected, for example, using a number of tools including CFD, bench testing and/or in vivo studies. Operating between 1000-1800 RPM, device 10, including fiber bundle section 200 could deliver flows from 1 to 3 liters per minute or LPM while generating pressure heads up to 280 mmHg. Operating between 700-2100 RPM, device 10, including fiber bundle section 200a could deliver flows from 0.25 to 4 liters per minute or LPM while generating pressure heads up to 410 mmHg. These dynamic ranges enable devices 10 hereof to be attached using peripheral and/or central placement modes using either access cannula or directly connecting grafts.

Velocity in fiber bundle 300 or 300a governs the gas exchange efficiency as mass transfer in general is enhanced in high velocity environments. However, attaining relatively high velocities can induce hemolysis if not well controlled. In device 10, velocity is controlled by specifying frontal/cross-sectional area of fiber bundles hereof to flow. This area is specified by the fiber bundle diameter. As described above, flow is normal to fibers. Fiber bundle diameters below 3 inches (or below 2.5 inches) may increase efficiency. A generally cylindrical bundle having a diameter of 3 inches corresponds to a frontal area or cross-sectional area of 7.07 $in^2$, while a diameter of 2.5 inches corresponds to a frontal area or cross-sectional area of 4.9 $in^2$. In a number of embodiments, the diameter may be no more than 2 inches (cross-sectional area of 3.14 $in^2$). In a number of studies, the diameter of fiber bundles 300 and 300a was each 1.75 inch, corresponding to a frontal or cross-sectional area of 2.41 $in^2$, which provides an increased level of efficiency. As diameter is decreased, fewer fibers are able to fit in a single layer of fibers. Thus the number of fiber layers must be increased, which increases the height of a particular bundle, to achieve a predetermined rate of gas exchange. As described above, in a number of embodiments, the diameter of the fiber bundle is maintained constant between different fiber bundle sections. The length of fiber bundle may be determined for a particular use to provide sufficient fiber bundle surface area for that use. The diameter of a fiber bundle hereof may, for example, be chosen based on the desired mean velocity of blood through fiber bundle. Based on the predetermined diameter and fiber density of the fiber bundle, the number of sheets or the length of the fiber bundle may be chosen to obtain a desired surface area. Mean velocity, as used herein, is defined as flowrate through device 10 divided by the cross-sectional area of the fiber bundle.

Polymethyl Pentene (PMP) fibers used in studies hereof had an outer diameter or OD of 380 micron and an inner diameter or ID of 200 micron. Many other materials can be used for the fibers hereof (for example, polymeric materials such as polypropylene, silicone, etc.). Such fibers may be coated and/or functionalized with a wide variety of materials. These fibers were manufactured as arrays, membranes or fabrics of hollow fibers, wherein a plurality of fibers is fabricated as an integral, generally planar array having generally the same fiber orientation. In forming fiber bundle 300 and other fiber bundles hereof, such arrays, membranes or fabrics are cut into sheets that were placed one on top of the other in stack of multiple layers as described above. The porosity of fiber bundle was maintained at approximately 0.5.

Figure 6A:
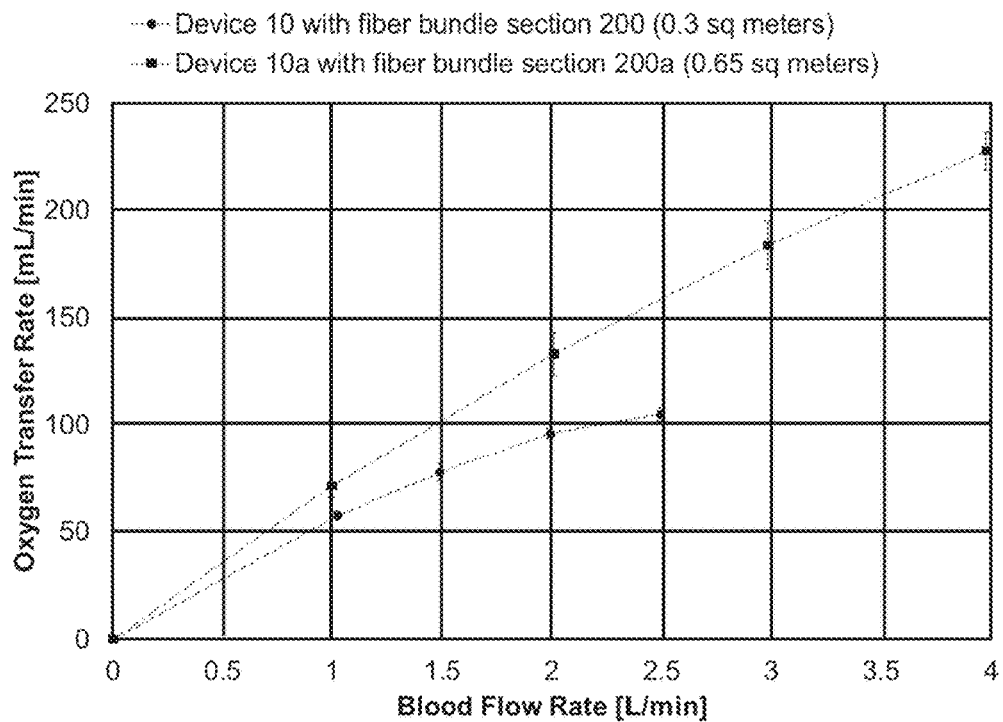
FIG. 6A illustrates data from studies of volumetric oxygenation rate (mL/min) as a function of flow rate for a device hereof with a smaller, pediatric fiber bundle section 200 as illustrated in FIG. 1A (0.3 $m^2$ total fiber surface area) and for a device hereof with a larger, adult fiber bundle section 200a as illustrated in FIG. 1B (0.65 $m^2$ total fiber surface area).

FIG. 6A illustrates a study of volume oxygenation rate (mL/min) as a function of blood flow rate (mL/min) for device 10 including fiber bundle section 200 and fiber bundle section 200a. As expected, the lower total fiber surface area (0.3 m$^2$) of fiber bundle 300 of fiber bundle section 200 results in lower oxygenation than fiber bundle 300a (having a total fiber surface area of 0.65 m$^2$) of fiber bundle section 200a. Device 10 with fiber bundle section 200a (designed for adult use) provides favorably comparable performance with existing devices designed for adult use, while device 10 with fiber bundle section 200 (designed for pediatric use) provide favorably comparable performance with existing devices for pediatric use.

Figure 6B:
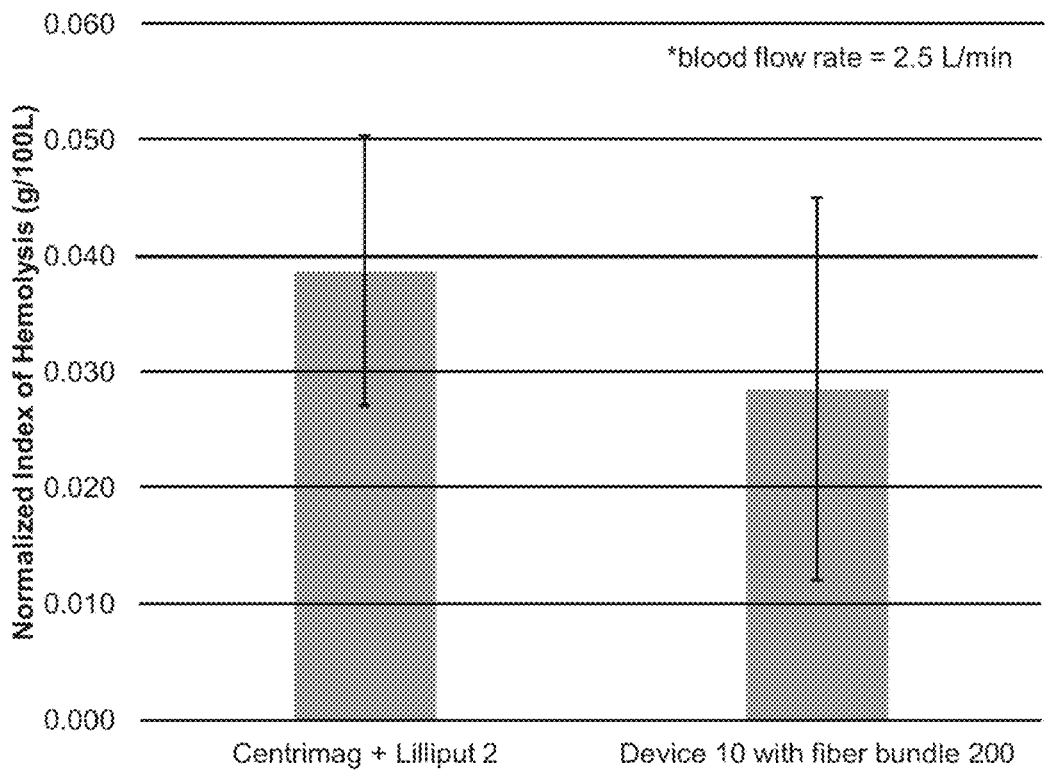
FIG. 6B illustrates a normalized index of hemolysis or NIH (g/100 L) for a device hereof with a smaller, pediatric fiber bundle section 200 as illustrated in FIG. 1A and for a commercially available control system (that is, the LILLI-PUT pediatric oxygenator available from Sorin Group of Modena, Italy with a CENTRIMAG® blood pump available from Thoratec Corporation of Pleasanton, California) at a flow rate of 2.5 L/min.

FIG. 6B provides the results of in-vitro hemolysis studies in the form of a normalized index of hemolysis or NIH (g/100 L) for a device hereof with a pediatric fiber bundle section 200 as illustrated in FIG. 1A and for a commercially available control system (that is, the LILLIPUT 2 pediatric oxygenator available from Sorin Group of Modena, Italy with a CENTRIMAG® blood pump available from Thoratec Corporation of Pleasanton, California) at a flow rate of 2.5 L/min.

In hemolysis studies, samples were drawn every 30 min to measure hematocrit (HCT) and plasma-free hemoglobin (pfHb). Plasma was isolated from whole blood in two centrifuge spins (15 min at 800 g, 10 min at 7200 g), and absorbance at 540 nm was measured spectrophotometrically (Genesys 10S UV-Vis; Thermo Scientific. Waltham, MA). PfHb concentration was calculated from absorbance using a standard curve developed from a linear-fit of serially diluted whole blood with 100% hemolysis versus absorbance.

The normalized index of hemolysis (NIH) was calculated for circuit comparisons:

$$NIH(g/100\ L)=\Delta pfHb/\Delta t\times V\times(100-HCT)/100\times 100/Q$$

Where NIH=normalized index of hemolysis in grams of hemoglobin released into the blood per 100 L of flow through the circuit (g/100 L); ΔpfHb=increase in pfHb over the sampling time interval (g/L); V=circuit volume (L); HCT=hematocrit (%); Δt=sampling time interval (min); Q=average blood flow rate (L/min).

Figure 6C:
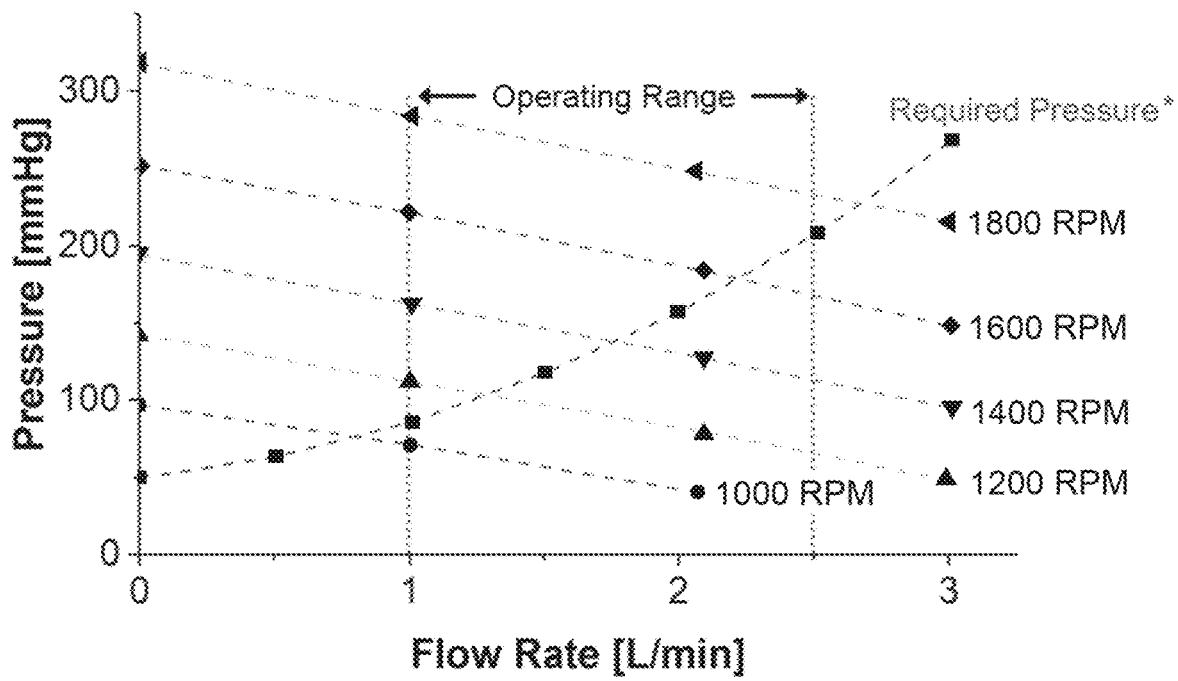
FIG. 6C illustrates a study of pressure as a function of flow rate for a device hereof with a smaller, pediatric fiber bundle section 200 assuming an 18 Fr (French) venous cannula, a 14 Fr arterial cannula and an outflow (pulmonary artery) pressure of 50 mmHg as a result of pulmonary hypertension.
Figure 6D:
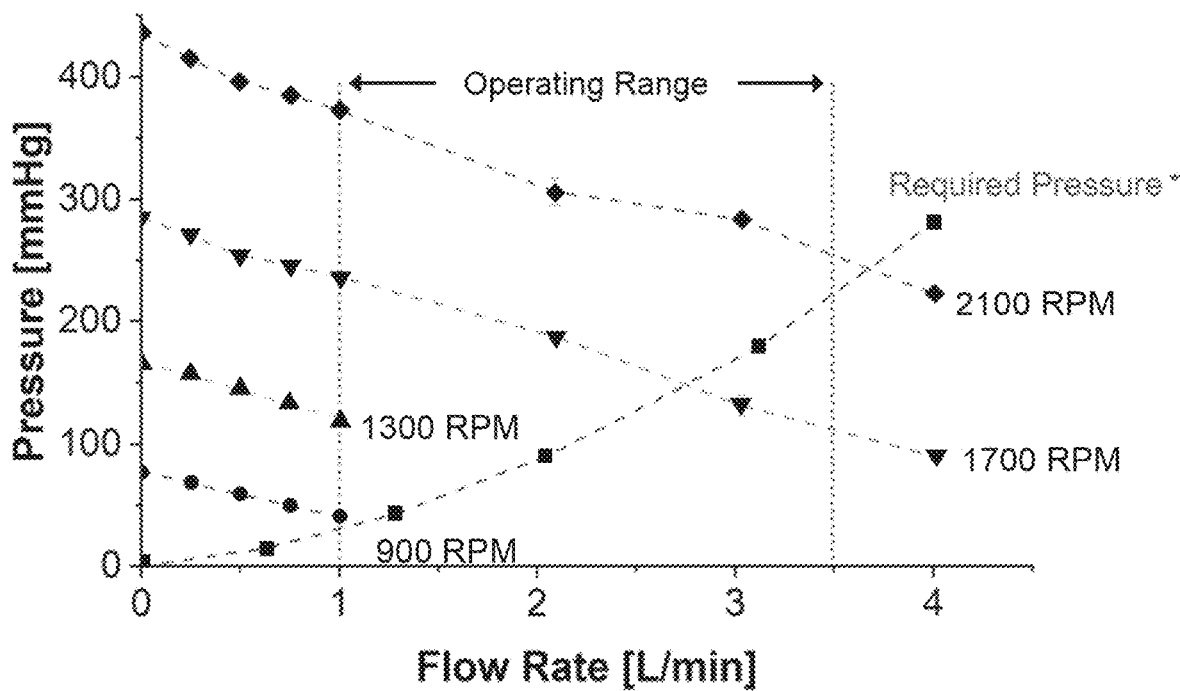
FIG. 6D illustrates a study of pressure as a function of flow rate for a device hereof with a larger, adult fiber bundle section 200*a* assuming a 27 Fr (French) dual-lumen cannula.
Figure 6E:
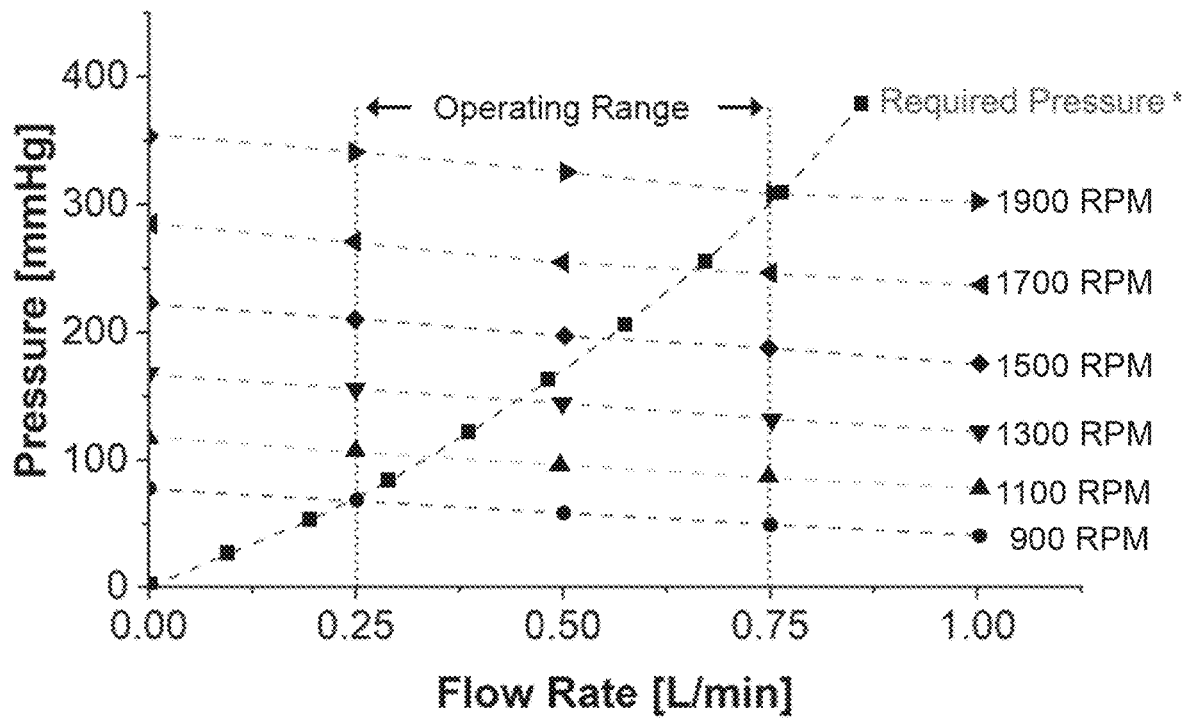
FIG. 6E illustrates a study of pressure as a function of flow rate for a device hereof with a larger, adult fiber bundle section 200*a* assuming a 15.5 Fr (French) dual-lumen cannula.
Figure 6F:
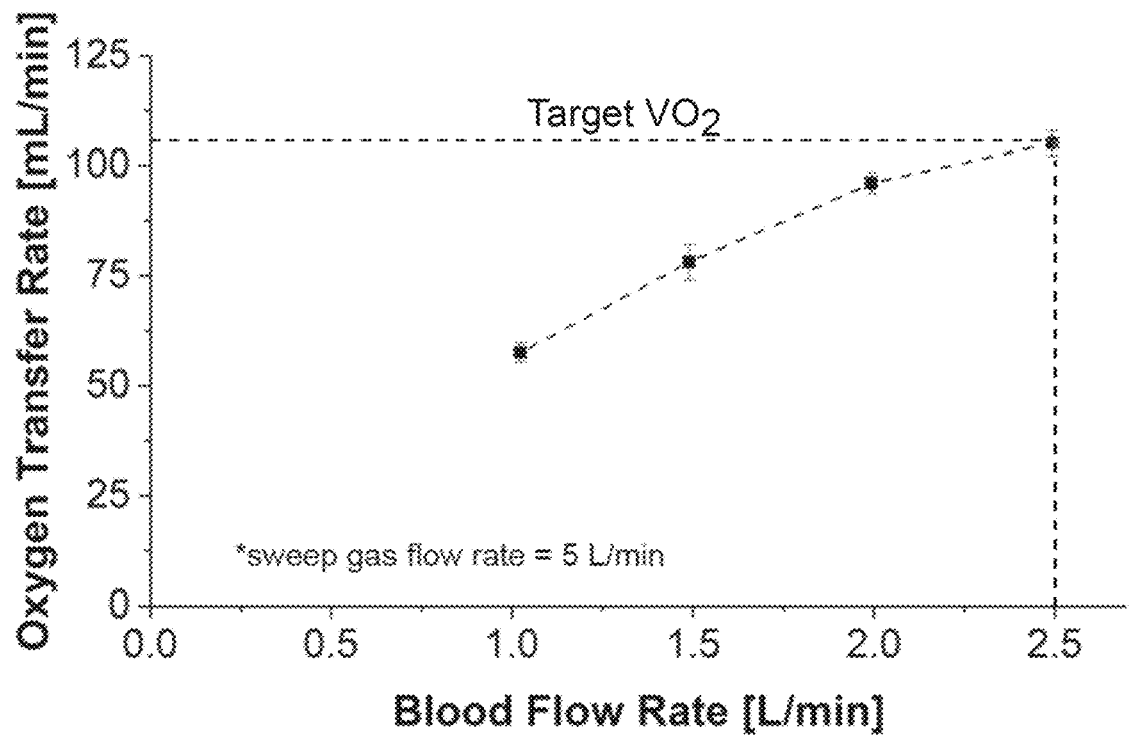
FIG. 6F illustrates a study of oxygen transfer rate as function of blood flow rate for a device hereof with a smaller, pediatric fiber bundle section 200.
Figure 6G:
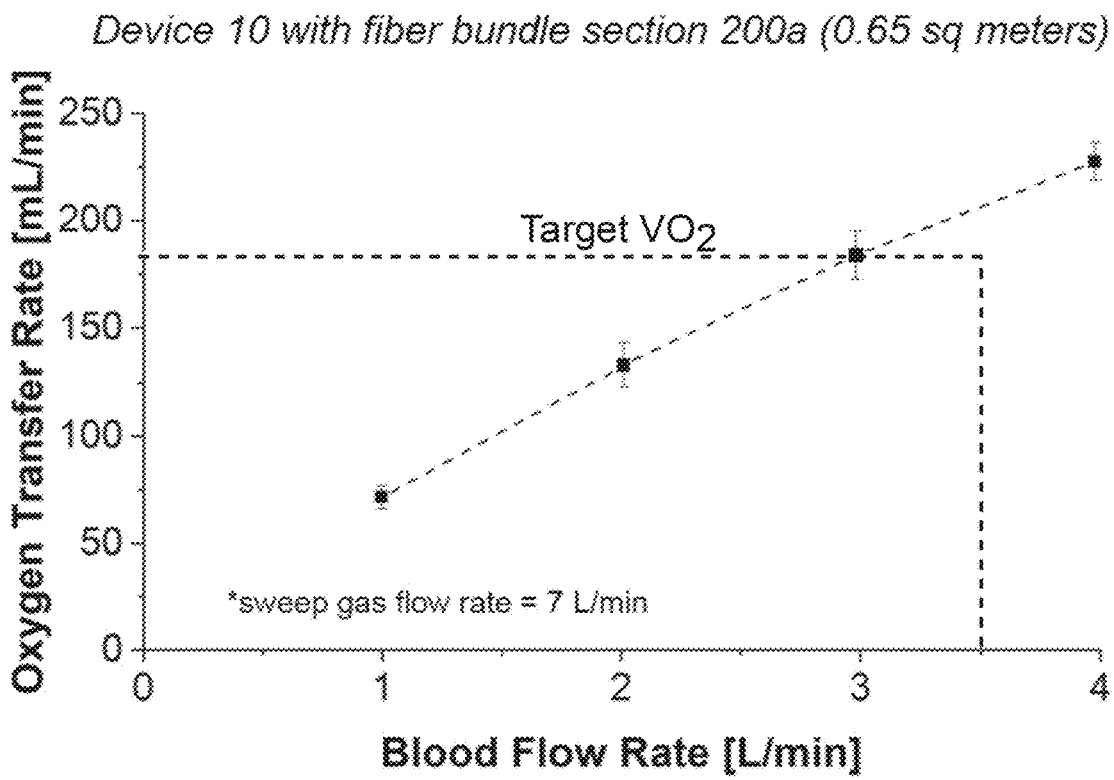
FIG. 6G illustrates a study of oxygen transfer rate as function of blood flow rate for a device hereof with a larger, adult fiber bundle section 200*a*.
Figure 6H:
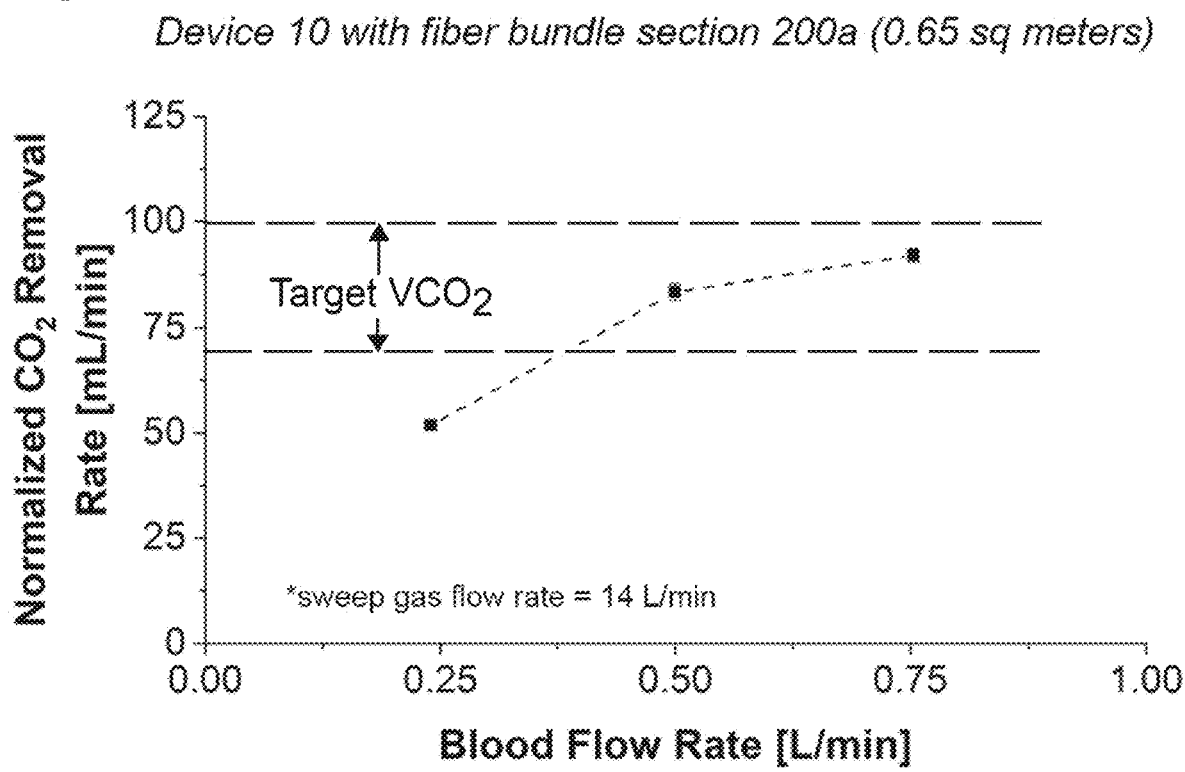
FIG. 6H illustrates a study of normalized $CO_2$ removal rate as function of blood flow rate for a device hereof with a larger, adult fiber bundle section 200*a*.

FIGS. 6C through 6H illustrate further pumping and gas exchange studies of devices hereof with pediatric fiber bundle section 200 and adult fiber bundle section 200a. The pump testing was performed using a blood analog solution (a carboxymethyl cellulose solution) that has a similar viscosity to blood. These benchtop results of FIGS. 6C through 6H demonstrate that the devices hereof are capable of producing suitable flow rates and gas exchange over a wide variety of lung treatment scenarios. FIG. 6C illustrates a study of pressure as a function of flow rate for a device hereof with a pediatric fiber bundle section 200 assuming an 18 Fr (French) venous cannula, a 14 Fr arterial cannula and an outflow (pulmonary artery) pressure of 50 mmHg as a result of pulmonary hypertension. FIG. 6D illustrates a study of pressure as a function of flow rate for a device hereof with an adult fiber bundle section 200a assuming a 27 Fr (French) dual-lumen cannula. FIG. 6E illustrates a study of pressure as a function of flow rate for a device hereof with an adult fiber bundle section 200a assuming a 15.5 Fr (French) dual-lumen cannula. FIGS. 6C through 6E demonstrate that the devices hereof are able to produce adequate blood flow rates for use in a variety of applications. For example, FIG. 6C demonstrates that the devices 10 hereof (including pediatric fiber bundle section 200) are able to generate the required pressure for flow rates and cannula sizes that would typically be used for pediatric respiratory support. Similarly, FIG. 6D demonstrates that the devices 10 hereof (including adult fiber bundle section 200a) are able to generate the required pressure for flow rates and cannula sizes that would typically be used for adult respiratory support. FIGS. 6F through 6H demonstrate that the devices hereof can achieve targeted oxygen and $CO_2$ transfer rates for a variety of applications. In that regard, FIG. 6F illustrates a study of oxygen transfer rate as function of blood flow rate for a device hereof with a pediatric fiber bundle section 200. FIG. 6G illustrates a study of oxygen transfer rate as function of blood flow rate for a device hereof with an adult fiber bundle section 200a. The data of FIGS. 6F and 6G are also set forth in FIG. 6A for comparison. FIG. 6H illustrates a study of normalized $CO_2$ removal rate as function of blood flow rate for a device hereof with an adult fiber bundle section 200a.

Figure 7A:
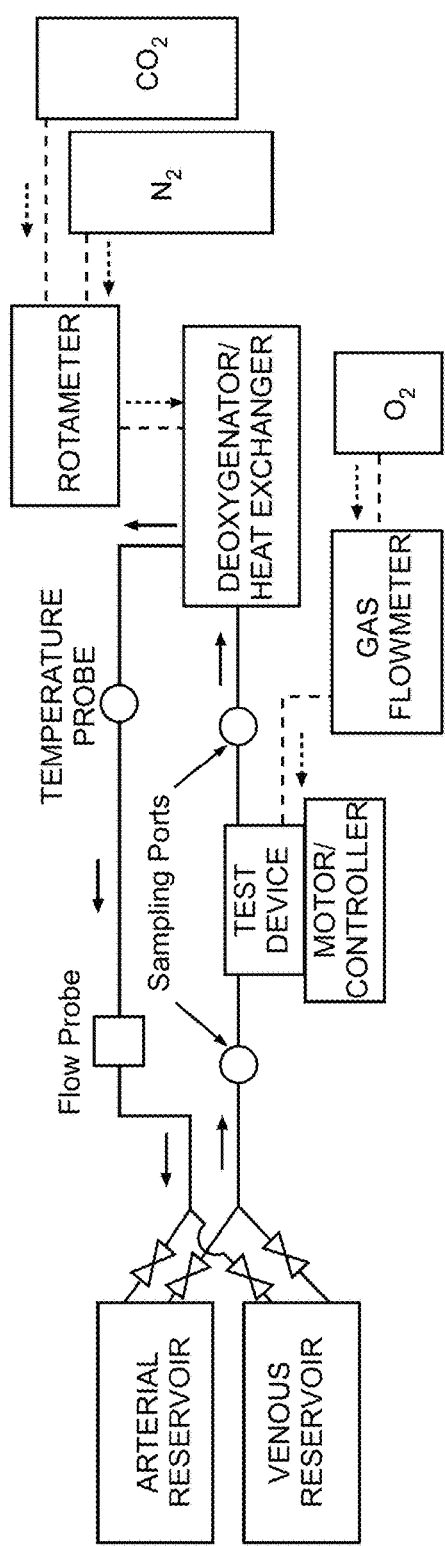
FIG. 7A illustrates a blood flow loop used in oxygenation or oxygen transfer rate studies hereof.
Figure 7B:
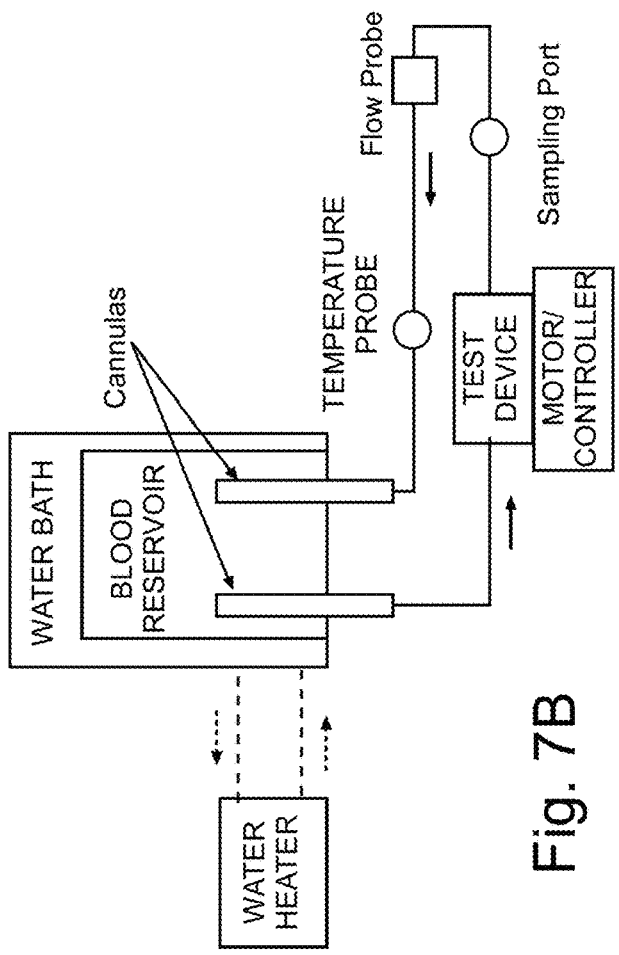
FIG. 7B illustrates a blood flow loop used in hemolysis studies hereof.

A blood/test fluid flow loop used in gas exchange (oxygenation/$CO_2$ removal) studies hereof is illustrated in FIG. 7A, while a blood flow loop used in hemolysis studies hereof is illustrated in FIG. 7B. In vitro oxygen exchange rates were, for example, measured in bovine blood using the experimental circuit of FIG. 7A. Prior to use, blood was filtered (40-μm filter, Pall Biomedical Inc., Fajardo, PR) and treated with heparin (15 IU/mL) and gentamicin (0.1 mg/mL). Blood was first pre-conditioned to venous conditions ($O_2$ saturation=65±5%, p$CO_2$=45±5 mmHg) via recirculation through a deoxygenator. Once venous blood conditions were achieved, sweep gas to the deoxygenator was discontinued and tubing was clamped to produce single-pass blood flow through the test device for oxygen exchange rate measurements. Blood temperature was maintained at 37±1 C throughout the experiment via a heat exchanger. Oxygen exchange rates were evaluated at varying blood flow rates and impeller rotation rates. Pure oxygen was used as the sweep gas and controlled using a GR series mass flow controller (Fathom Technologies, Georgetown, TX). Blood samples were taken at the inlet and outlet of the test device and analyzed using a RAPIDPoint 405 blood gas analyzer with co-oximetry (Siemens Healthcare Diagnostics Inc., Tarrytown, NY). Oxygen exchange rates were calculated from inlet and outlet oxygen partial pressures and saturations using the following equation $$\dot{V}_{O_2}=Q[a_{O_2}(P_{O_2}^{out}-P_{O_2}^{in})+10 C_t Hgb(S_{O_2}^{out}-S_{O_2}^{in})]$$

where $\dot{V}_{O_2}$ is the oxygen exchange rate (mL/min), Q is the blood flow rate (L/min), $a_{O_2}$ is the solubility of oxygen in blood [3E-2 mL $O_2$/(L blood·mmHg)], $P_{O_2}^{out}-P_{O_2}^{in}$ is the oxygen partial pressure difference across the device (mmHg), $C_t$ is the hemoglobin binding capacity (1.34 mL $O_2/g$), Hgb is the hemoglobin concentration (g/dL), and $S_{O_2}^{out}-S_{O_2}^{in}$ is the fractional oxygen saturation difference across the device.

Blood damage was evaluated at varying flow rates using bovine blood. Prior to use, blood was filtered (40-µm filter, Pall Biomedical Inc., Fajardo, PR) and treated with heparin (15 IU/mL) and gentamicin (0.1 mg/mL). Evaluation was performed using a continuous flow circuit (schematic shown below) consisting of the test device connected to an 800-mL compliant blood reservoir via the intended use cannulas. The compliant reservoir was submerged within a heated water bath during testing to maintain a blood temperature of 37±1 C. For each operating condition evaluated, blood (hematocrit=30%) was circulated for a period of 6 hours during which blood samples were collected every 30 minutes. Plasma was isolated from whole blood in two centrifuge spins (15 min at 800 g, 10 min at 7200 g), and absorbance at 540 nm was measured spectrophotometrically (Genesys 10S UV-Vis; Thermo Scientific, Waltham, MA). PfHb concentration was calculated from absorbance using a standard curve developed from a linear-fit of serially diluted whole blood with 100% hemolysis versus absorbance.

Unlike many devices, devices 10 hereof may be used in both relatively high flow rate respiratory support/oxygenation and relatively lower flow rate carbon dioxide removal. In the case of pediatric respiratory support with fiber bundle section 200, the blood flow rate may, for example, be in the range of approximately 1 to approximately 2.5 L/min. An 18-22 Fr (French) venous cannula or a 12-16 Fr arterial cannula may be used. In the case of adult respiratory support with fiber bundle section 200a, the blood flow rate may, for example, be in the range of approximately 1 to approximately 3.5 L/min. A 27 Fr dual lumen cannula may be used. In the case of low flow carbon dioxide removal or $ECCO_2R$ with fiber bundle section 200a, the flow rate may, for example, be less than 1 L/min. Further a 15.5 Fr dual lumen cannula may be used. A clinician may, for example, begin a patient with a cannula and a flow rate for $ECCO_2R$ and later discover that further intervention (oxygenation) is required. Full respiratory support, including oxygenation and carbon dioxide removal, may, for example, be initiated by changing the cannula to a larger cannula and increasing flow rate without the necessity of using a different device or the necessity of changing the fiber bundle section of the device. The devices hereof thus span the range of low flow rate to provide carbon dioxide removal to high flow rate to provide oxygenation and carbon dioxide removal without changing either the base section (including the pumping mechanism) of the fiber bundle section, thereby providing use among different patients as well as changing course of treatment for a particular patient.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A system for lung assist, comprising:
a plurality of separate fiber bundle sections, each of the fiber bundle sections comprising a fiber bundle housing defining a fiber bundle compartment therein, a fiber bundle positioned within the fiber bundle compartment, the fiber bundle comprising a plurality of hollow gas permeable fibers, the plurality of hollow gas permeable fibers being adapted to permit diffusion of gas between blood and an interior of the plurality of hollow gas permeable fibers, the plurality of hollow gas permeable fibers being positioned such that blood flows around the plurality of hollow gas permeable fibers when flowing through the fiber bundle compartment, the fiber bundle of each of the plurality of fiber bundle sections being different in at least one property from the fiber bundle of each of the other of the plurality of fiber bundle sections, each fiber bundle housing further comprising a gas inlet in fluid connection with the fiber bundle housing and in fluid connection with inlets of the plurality of hollow gas permeable fibers, a gas outlet in fluid connection with the fiber bundle housing and in fluid connection with outlets of the plurality of hollow gas permeable fibers, a blood outlet in fluid connection with a first end of the fiber bundle housing, and a first interface disposed on a second end of the fiber bundle housing opposite the first end, and
a base section comprising a housing comprising a pressurizing section including a pressurizing compartment and an interface section, the interface section including an extending section which is positioned at a lateral end of the pressurizing section and extends at an angle from the lateral end of the pressurizing section and a second interface formed on the extending section and configured to form a releasable, sealing connection with the first interface of one of the plurality of fiber bundle sections such that the fiber bundle housing of the one of the plurality of fiber bundle sections extends substantially parallel to the pressurizing section, wherein the base section housing and the fiber bundle housing are separate elements connected by the releasable, sealing connection between the first and second interfaces, the pressurizing section further including a pressurizing mechanism within the pressurizing compartment, a blood inlet in fluid connection with the pressurizing compartment and a conduit in fluid connection with the pressurizing compartment at a first end thereof via which pressurized fluid exits the pressurizing compartment, wherein a second end of the conduit is placed in fluid connection with a second end of the fiber bundle when the fiber bundle housing of the fiber bundle section is connected to the housing of the base section via the first interface and the second interface.

2. The system of claim 1 wherein the pressurizing mechanism comprises an impeller rotatable within the pressurizing compartment.

3. The system of claim 2 wherein the extending section extends from the pressurizing section at an angle of 90 degrees, wherein the conduit comprises a flow channel which extends through the extending section.

4. The system of claim 3 wherein the flow channel is in fluid connection with a manifold formed in the extending section.

5. The system of claim 4 wherein the extending section extends in a plane generally perpendicular to a plane of rotation of the impeller.

6. The system of claim 5 wherein the first interface of each of the fiber bundle sections attaches to the second interface of the base section so that the axis of the fiber bundle of the one of the plurality of fiber bundle sections attached to the base section is oriented generally parallel to a plane of rotation of the impeller.

7. The system of claim 6 wherein the one of the plurality of fiber bundle sections attached to the base section is positioned over the pressurizing compartment of the base section.

8. The system of claim 7 wherein bulk flow of blood through the fiber bundle is in a generally axial direction.

9. The system of claim 1 wherein the plurality of hollow gas permeable fibers of each of the fiber bundles extend generally perpendicular to the direction of bulk flow of blood through the fiber bundle from the second end of the fiber bundle to the first end of the fiber bundle.

10. The system of claim 1 wherein the plurality of hollow gas permeable fibers is formed in at least one generally cylindrical bundle.

11. The system of claim 10 wherein the generally cylindrical bundle is formed from a plurality of layers of fiber fabric, each of the plurality of layers of fiber fabric comprising hollow gas permeable fibers.

12. The system of claim 1 wherein the plurality of fiber bundle sections differ from each other in length and thereby different fiber surface areas.

13. The system of claim 12 wherein at least one of the plurality of fiber bundle sections is configured for use with pediatric patients and at least one of the plurality of fiber bundle sections is configured for use with adult patients.

14. The system of claim 1 wherein at least one combination of one of the plurality of fiber bundle sections and the base section is suitable for carbon dioxide removal in a first range of flow rates and is suitable for oxygenation and carbon dioxide removal in a second range of flow rates, wherein the second range of flow rates extends to higher flow rates.

15. A method of providing extracorporeal lung assist to a patient, comprising:
providing a plurality of separate fiber bundle sections, each of the fiber bundle sections comprising a fiber bundle housing defining a fiber bundle compartment therein, a fiber bundle positioned within the fiber bundle compartment, the fiber bundle comprising a plurality of hollow gas permeable fibers, the plurality of hollow gas permeable fibers being adapted to permit diffusion of gas between blood and an interior of the plurality of hollow gas permeable fibers, the plurality of hollow gas permeable fibers being positioned such that blood flows around the plurality of hollow gas permeable fibers when flowing through the fiber bundle compartment, the fiber bundle of each of the plurality of fiber bundle sections being different in at least one property from the fiber bundle of each of the other of the plurality of fiber bundle sections, each fiber bundle housing further comprising a gas inlet in fluid connection with the fiber bundle housing and in fluid connection with inlets of the plurality of hollow gas permeable fibers, a gas outlet in fluid connection with the fiber bundle housing and in fluid connection with outlets of the plurality of hollow gas permeable fibers, a blood outlet in fluid connection with a first end of the fiber bundle housing, and a first interface disposed on a second end of the fiber bundle housing opposite the first end,
providing a base section comprising a housing comprising a pressurizing section including a pressurizing compartment and an interface section, the interface section including an extending section which is positioned at a lateral end of the pressurizing section and extends at an angle from the lateral end of the pressurizing section and a second interface formed on the extending section and configured to form a releasable, sealing connection with the first interface of one of the plurality of fiber bundle sections such that the fiber bundle housing of the one of the plurality of fiber bundle sections extends substantially parallel to the pressurizing section, wherein the base section housing and the fiber bundle housing are separate elements connected by the releasable, sealing connection between the first and second interfaces, the pressurizing section further including a pressurizing mechanism within the pressurizing compartment, a blood inlet in fluid connection with the pressurizing compartment and a conduit in fluid connection with the pressurizing compartment at a first end thereof via which pressurized fluid exits the pressurizing compartment, wherein a second end of the conduit is placed in fluid connection with a second end of the fiber bundle when the fiber bundle housing of the fiber bundle section is connected to the housing of the base section via the first interface and the second interface; and
attaching one of the plurality of fiber bundle sections to the base section via connection of the first interface and the second interface, wherein the fiber bundle of the one of the fiber bundle sections is chosen for the patient.

16. The method of claim 15 wherein the plurality of hollow gas permeable fibers is formed in at least one generally cylindrical bundle.

17. The method of claim 16 wherein the first interface of each of the fiber bundle sections attaches to the second interface of the base section so that the axis of the fiber bundle of the one of the plurality of fiber bundle sections attached to the base section is oriented generally parallel to a plane of rotation of an impeller rotatable within the pressurizing compartment.

18. The method of claim 17 wherein the one of the plurality of fiber bundle sections attached to the base section is positioned over the pressurizing compartment of the base section.

19. The method of claim 15 wherein the plurality of fiber bundle sections comprise fiber bundle sections of different lengths comprising fiber bundles of different lengths and thereby different fiber surface areas.

20. A system for lung assist, comprising:
a fiber bundle section comprising a fiber bundle housing defining a fiber bundle compartment therein, a fiber bundle positioned within the fiber bundle compartment, the fiber bundle comprising a plurality of hollow gas permeable fibers, the plurality of hollow gas permeable fibers being adapted to permit diffusion of gas between blood and an interior of the plurality of hollow gas permeable fibers, the plurality of hollow gas permeable fibers being positioned such that blood flows around the plurality of hollow gas permeable fibers when flowing through the fiber bundle compartment, the fiber bundle housing further comprising a gas inlet in fluid connection with the fiber bundle housing and in fluid connection with inlets of the plurality of hollow gas permeable fibers, a gas outlet in fluid connection with the fiber bundle housing and in fluid connection with outlets of the plurality of hollow gas permeable fibers, a blood outlet in fluid connection with a first end of the fiber bundle housing and a first interface disposed on a second end of the fiber bundle housing opposite the first end, and
a base section comprising a housing comprising a pressurizing section including a pressurizing compartment and an interface section, the interface section including an extending section which is positioned at a lateral end of the pressurizing section and extends at an angle from the lateral end of the pressurizing section and a second interface formed on the extending section and configured to form a releasable, sealing connection with the first interface of the fiber bundle section such that the fiber bundle housing of the fiber bundle section extends substantially parallel to the pressurizing section, wherein the base section housing and the fiber bundle housing are separate elements connected by the releasable, sealing connection between the first and second interfaces, a pressurizing mechanism within the pressurizing compartment, a blood inlet in fluid connection with the pressurizing compartment and a conduit in fluid connection with the pressurizing compartment at a first end thereof via which pressurized fluid exits the pressurizing compartment, wherein a second end of the conduit is placed in fluid connection with a second end of the fiber bundle when the fiber bundle housing of the fiber bundle section is connected to the housing of the base section via the first interface and the second interface.

* * * * *